(12) United States Patent
Petrochenko et al.

(10) Patent No.: US 11,311,695 B2
(45) Date of Patent: Apr. 26, 2022

(54) MEDICAL TUBES AND METHODS OF MANUFACTURE

(71) Applicant: Fisher & Paykel Healthcare Limited, Auckland (NZ)

(72) Inventors: Anton Petrochenko, Auckland (NZ); Wenjie Robin Liang, Auckland (NZ); Paul James Tonkin, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 151 days.

(21) Appl. No.: 16/472,770

(22) PCT Filed: Dec. 20, 2017

(86) PCT No.: PCT/IB2017/058182
§ 371 (c)(1),
(2) Date: Jun. 21, 2019

(87) PCT Pub. No.: WO2018/116187
PCT Pub. Date: Jun. 28, 2018

(65) Prior Publication Data
US 2020/0398014 A1 Dec. 24, 2020

Related U.S. Application Data

(60) Provisional application No. 62/438,281, filed on Dec. 22, 2016.

(51) Int. Cl.
*A61M 16/00* (2006.01)
*A61M 16/08* (2006.01)
*A61M 16/10* (2006.01)

(52) U.S. Cl.
CPC .... *A61M 16/0833* (2014.02); *A61M 16/0003* (2014.02); *A61M 16/0875* (2013.01);
(Continued)

(58) Field of Classification Search
CPC .......... A61M 16/0833; A61M 16/0003; A61M 16/1095; A61M 16/0875; A61M 2205/3368; A61M 2207/00
See application file for complete search history.

(56) References Cited

U.S. PATENT DOCUMENTS

| 485,127 | A | 10/1892 | Lynch |
| 2,073,335 | A | 3/1937 | Connell |

(Continued)

FOREIGN PATENT DOCUMENTS

| AU | 1448473 | 9/1976 |
| AU | 727989 | 6/2000 |

(Continued)

OTHER PUBLICATIONS

US 10,426,912 B2, 10/2019, Buswell et al. (withdrawn)
(Continued)

*Primary Examiner* — Steven O Douglas
(74) *Attorney, Agent, or Firm* — Knobbe, Martens, Olson & Bear, LLP

(57) ABSTRACT

Medical tubes and methods of manufacturing medical tubes. The tube(s) may be a composite structure made of two or more distinct components that are spirally wound to form an elongate tube. For example, one of the components may be a spirally wound elongate hollow body, and the other component may be an elongate structural component also spirally wound between turns of the spirally wound hollow body. The tube(s) need not be made from distinct components, however. For instance, an elongate hollow body formed (for example, extruded) from a single material may be spirally wound to form an elongate tube. The elongate hollow body itself may in transverse cross-section have a thin wall portion and a relatively thicker or more rigid reinforcement portion. The tube(s) can be incorporated into (Continued)

a variety of medical circuits or may be employed for other medical uses.

28 Claims, 30 Drawing Sheets

(52) U.S. Cl.
CPC . *A61M 16/1095* (2014.02); *A61M 2205/3368* (2013.01); *A61M 2207/00* (2013.01)

(56) References Cited

U.S. PATENT DOCUMENTS

| | | | |
|---|---|---|---|
| 2,516,864 A | 8/1950 | Gilmore et al. |
| 2,788,936 A | 4/1957 | Kemnitz |
| 2,874,722 A | 2/1959 | Hamblin |
| 3,117,596 A | 1/1964 | Khan |
| 3,163,707 A | 12/1964 | Darling |
| 3,283,580 A | 11/1966 | Jacob et al. |
| 3,394,954 A | 7/1968 | Sams |
| 3,495,628 A | 2/1970 | Boender |
| 3,582,968 A | 6/1971 | Buiting |
| 3,584,193 A | 6/1971 | Badertscher |
| 3,638,926 A | 2/1972 | Melville et al. |
| 3,695,267 A | 10/1972 | Hirtz et al. |
| 3,766,914 A | 10/1973 | Jacobs |
| 3,914,349 A | 10/1975 | Stipanuk |
| 3,926,223 A | 12/1975 | Petzetakis |
| 3,963,856 A | 6/1976 | Carlson et al. |
| 3,990,727 A | 11/1976 | Gallagher |
| 4,013,122 A | 3/1977 | Long |
| 4,013,742 A | 3/1977 | Lang |
| 4,033,808 A | 7/1977 | Petzetakis |
| 4,038,519 A | 7/1977 | Foucras |
| 4,038,980 A | 8/1977 | Fodor |
| 4,051,205 A | 9/1977 | Grant |
| 4,060,576 A | 11/1977 | Grant |
| 4,110,419 A | 8/1978 | Miller |
| 4,111,197 A | 9/1978 | Warncke et al. |
| 4,160,466 A | 7/1979 | Jousson |
| 4,172,105 A | 10/1979 | Miller et al. |
| 4,301,200 A | 11/1981 | Langenfeld |
| 4,333,451 A | 6/1982 | Paluch |
| 4,428,403 A | 1/1984 | Lee et al. |
| 4,430,994 A | 2/1984 | Clawson et al. |
| 4,487,232 A | 12/1984 | Kanao |
| 4,490,575 A | 12/1984 | Kutnyak |
| 4,500,480 A | 2/1985 | Cambio, Jr. |
| 4,529,867 A | 7/1985 | Velnosky et al. |
| 4,531,551 A | 7/1985 | Eichelberger et al. |
| 4,553,023 A | 11/1985 | Jameson et al. |
| 4,574,188 A | 3/1986 | Midgley et al. |
| 4,597,917 A | 7/1986 | Lunsford |
| 4,621,632 A | 11/1986 | Bartels et al. |
| 4,640,804 A | 2/1987 | Mizoguchi |
| 4,676,237 A | 6/1987 | Wood et al. |
| 4,684,786 A | 8/1987 | Mann et al. |
| 4,686,354 A | 8/1987 | Makin |
| 4,695,955 A | 9/1987 | Faisandier |
| 4,708,831 A | 11/1987 | Elsworth et al. |
| 4,710,887 A | 12/1987 | Ho |
| 4,722,334 A | 2/1988 | Blackmer et al. |
| 4,753,758 A | 6/1988 | Miller |
| 4,773,448 A | 9/1988 | Francis |
| 4,780,247 A | 10/1988 | Yasuda |
| 4,829,781 A | 5/1989 | Hitzler |
| 4,829,997 A | 5/1989 | Douwens et al. |
| 4,829,998 A | 5/1989 | Jackson |
| 4,844,512 A | 7/1989 | Gahwiler |
| 4,861,523 A | 8/1989 | Beran |
| 4,903,736 A | 2/1990 | Baston et al. |
| 4,911,157 A | 3/1990 | Miller |
| 4,911,357 A | 3/1990 | Kitamura |
| 4,921,642 A | 5/1990 | LaTorraca |
| 4,941,469 A | 7/1990 | Adahan |
| 4,967,744 A | 11/1990 | Chua |
| 5,031,612 A | 7/1991 | Clementi |
| 5,062,145 A | 10/1991 | Zwaan et al. |
| 5,092,326 A | 3/1992 | Winn et al. |
| 5,101,820 A | 4/1992 | Christopher |
| 5,127,442 A | 7/1992 | Blomqvist |
| 5,148,801 A | 9/1992 | Douwens et al. |
| 5,164,652 A | 11/1992 | Johnson et al. |
| 5,213,376 A | 5/1993 | Szabo |
| 5,224,923 A | 7/1993 | Moffett et al. |
| 5,230,331 A | 7/1993 | Rusz et al. |
| 5,231,979 A | 8/1993 | Rose et al. |
| 5,336,156 A | 8/1994 | Miller et al. |
| 5,346,128 A | 9/1994 | Wacker |
| 5,347,211 A | 9/1994 | Jakubowski |
| 5,367,604 A | 11/1994 | Murray |
| 5,388,443 A | 2/1995 | Manaka |
| 5,392,770 A | 2/1995 | Clawson et al. |
| 5,404,729 A | 4/1995 | Matsuoka et al. |
| 5,405,269 A | 4/1995 | Stupecky |
| 5,428,752 A | 6/1995 | Goren et al. |
| 5,449,234 A | 9/1995 | Gipp et al. |
| 5,454,061 A | 9/1995 | Carlson |
| 5,482,031 A | 1/1996 | Lambert |
| 5,516,466 A | 5/1996 | Schlesch et al. |
| 5,529,060 A | 6/1996 | Salmon et al. |
| 5,537,996 A | 7/1996 | McPhee |
| 5,551,731 A | 9/1996 | Gray et al. |
| 5,558,084 A | 9/1996 | Daniell et al. |
| 5,564,415 A | 10/1996 | Dobson et al. |
| 5,588,423 A | 12/1996 | Smith |
| 5,591,292 A | 1/1997 | Blomqvist |
| 5,600,752 A | 2/1997 | Lopatinsky |
| 5,630,806 A | 5/1997 | Inagaki |
| 5,637,168 A | 6/1997 | Carlson |
| 5,640,951 A | 6/1997 | Huddart et al. |
| 5,673,687 A | 10/1997 | Dobson et al. |
| 5,759,149 A | 6/1998 | Goldberg et al. |
| 5,769,071 A | 6/1998 | Turnbull |
| 5,778,872 A | 7/1998 | Fukunaga et al. |
| 5,848,223 A | 12/1998 | Carlson |
| 5,906,201 A | 5/1999 | Nilson |
| 5,943,473 A | 8/1999 | Levine |
| 5,988,164 A | 11/1999 | Paluch |
| 5,991,507 A | 11/1999 | Bencsits |
| 6,010,118 A | 1/2000 | Milewicz |
| 6,024,694 A | 2/2000 | Goldberg et al. |
| 6,038,457 A | 3/2000 | Barkat |
| 6,050,260 A | 4/2000 | Daniell et al. |
| 6,078,730 A | 6/2000 | Huddart et al. |
| 6,095,505 A | 8/2000 | Miller |
| 6,105,649 A | 8/2000 | Levingston et al. |
| 6,109,782 A | 8/2000 | Fukura et al. |
| 6,125,847 A | 10/2000 | Lin |
| 6,138,674 A | 10/2000 | Gull et al. |
| 6,142,974 A | 11/2000 | Kistner et al. |
| 6,158,431 A | 12/2000 | Poole |
| 6,167,883 B1 | 1/2001 | Beran et al. |
| 6,189,870 B1 | 2/2001 | Withall |
| 6,190,480 B1 | 2/2001 | Carlson |
| 6,219,490 B1 | 4/2001 | Gibertoni et al. |
| 6,272,933 B1 | 8/2001 | Gradon et al. |
| 6,311,958 B1 | 11/2001 | Stanek |
| 6,347,646 B2 | 2/2002 | Fukui et al. |
| 6,349,722 B1 | 2/2002 | Gradon et al. |
| 6,367,472 B1 | 4/2002 | Koch |
| 6,367,510 B1 | 4/2002 | Carlson |
| 6,374,864 B1 | 4/2002 | Philip |
| 6,384,755 B1 | 5/2002 | Hayden |
| 6,394,084 B1 | 5/2002 | Nitta |
| 6,394,145 B1 | 5/2002 | Bailly |
| 6,397,841 B1 | 6/2002 | Kenyon et al. |
| 6,397,846 B1 | 6/2002 | Skog et al. |
| 6,398,197 B1 | 6/2002 | Dickinson et al. |
| 6,463,925 B2 | 10/2002 | Nuckols et al. |
| 6,474,335 B1 | 11/2002 | Lammers |
| 6,537,405 B1 | 3/2003 | Henderson et al. |
| 6,540,734 B1 | 4/2003 | Chiu et al. |
| 6,543,412 B2 | 4/2003 | Amou et al. |

(56) References Cited

U.S. PATENT DOCUMENTS

| | | |
|---|---|---|
| 6,564,011 B1 | 5/2003 | Janoff et al. |
| 6,584,972 B2 | 7/2003 | McPhee |
| 6,594,366 B1 | 7/2003 | Adams |
| 6,668,828 B1 | 12/2003 | Figley et al. |
| 6,691,707 B1 | 2/2004 | Gunaratnam et al. |
| 6,694,974 B1 | 2/2004 | George-Gradon et al. |
| 6,718,974 B1 | 4/2004 | Moberg |
| 6,827,109 B2 | 12/2004 | Mccaughtry |
| 6,918,389 B2 | 7/2005 | Seakins et al. |
| 6,932,119 B2 | 8/2005 | Carlson |
| 6,953,354 B2 | 10/2005 | Edirisuriya et al. |
| 7,086,422 B2 | 8/2006 | Huber et al. |
| 7,096,864 B1 | 8/2006 | Mayer et al. |
| 7,120,354 B2 | 10/2006 | Mackie et al. |
| 7,140,367 B2 | 11/2006 | White et al. |
| 7,156,127 B2 | 1/2007 | Moulton et al. |
| 7,157,035 B2 | 1/2007 | Edirisuriya et al. |
| 7,291,240 B2 | 11/2007 | Smith et al. |
| 7,468,116 B2 | 12/2008 | Smith et al. |
| 7,559,324 B2 | 7/2009 | Smith et al. |
| 7,588,029 B2 | 9/2009 | Smith et al. |
| 7,588,186 B2 | 9/2009 | Steffen et al. |
| 7,637,288 B2 | 12/2009 | Huber et al. |
| 7,647,926 B2 | 1/2010 | Gerder et al. |
| 7,766,050 B2 | 8/2010 | Patel |
| 7,814,907 B2 | 10/2010 | Bremner et al. |
| 7,870,857 B2 | 1/2011 | Dhuper et al. |
| 7,965,930 B2 | 6/2011 | Carlson et al. |
| 7,983,542 B2 | 7/2011 | Mcghin et al. |
| 7,997,267 B2 | 8/2011 | Ging et al. |
| 8,091,547 B2 | 1/2012 | Thudor et al. |
| 8,122,882 B2 | 2/2012 | Mcghin et al. |
| 8,186,345 B2 | 5/2012 | Payton et al. |
| 8,235,041 B2 | 8/2012 | Seakins et al. |
| 8,253,076 B2 | 8/2012 | Andel et al. |
| 8,333,194 B2 | 12/2012 | Lewis et al. |
| 8,333,199 B2 | 12/2012 | Landis et al. |
| 8,360,059 B2 | 1/2013 | Koulechov et al. |
| 8,453,641 B2 | 6/2013 | Payton et al. |
| 8,459,259 B2 | 6/2013 | Klasek et al. |
| 8,469,025 B2 | 6/2013 | Mayer et al. |
| 8,511,305 B2 | 8/2013 | Liu et al. |
| 8,511,651 B2 | 8/2013 | Fridberg et al. |
| 8,522,782 B2 | 9/2013 | Lewis et al. |
| 8,563,863 B2 | 10/2013 | Carlson |
| 8,563,864 B2 | 10/2013 | Carlson |
| 8,631,789 B2 | 1/2014 | Virr et al. |
| 8,709,187 B2 | 4/2014 | Smith et al. |
| 8,733,349 B2 | 5/2014 | Bath et al. |
| 8,844,522 B2 | 9/2014 | Huby et al. |
| 9,119,933 B2 | 9/2015 | Bedford et al. |
| 9,440,040 B2 | 9/2016 | Klasek et al. |
| 9,517,321 B2 | 12/2016 | Buechi et al. |
| 9,555,210 B2 | 1/2017 | Seakins et al. |
| 9,572,949 B2 | 2/2017 | Vos et al. |
| 9,855,398 B2 | 1/2018 | Klasek et al. |
| 10,080,866 B2 | 9/2018 | Stoks et al. |
| 10,589,050 B2 | 3/2020 | Buswell et al. |
| 10,960,167 B2 | 3/2021 | Liu et al. |
| 11,129,954 B2 | 9/2021 | Buswell et al. |
| 2001/0017134 A1 | 8/2001 | Bahr |
| 2001/0050080 A1 | 12/2001 | Seakins et al. |
| 2002/0038392 A1 | 3/2002 | De La Huerga |
| 2002/0120236 A1 | 8/2002 | Diaz et al. |
| 2002/0124847 A1 | 9/2002 | Smith et al. |
| 2002/0173717 A1 | 11/2002 | Rohling et al. |
| 2002/0186966 A1 | 12/2002 | Zimmer et al. |
| 2003/0059213 A1 | 3/2003 | Mackie et al. |
| 2003/0183294 A1 | 10/2003 | Carlson |
| 2003/0236015 A1 | 12/2003 | Edirisuriya et al. |
| 2004/0074493 A1 | 4/2004 | Seakins et al. |
| 2004/0074495 A1 | 4/2004 | Wickham et al. |
| 2004/0079371 A1 | 4/2004 | Gray |
| 2004/0081784 A1 | 4/2004 | Smith et al. |
| 2004/0099268 A1 | 5/2004 | Smith et al. |
| 2004/0101026 A1 | 5/2004 | Nitta et al. |
| 2004/0149284 A1 | 8/2004 | Smith et al. |
| 2004/0182392 A1 | 9/2004 | Gerder et al. |
| 2004/0244858 A1 | 12/2004 | Jeong |
| 2005/0059957 A1 | 6/2005 | Byerly et al. |
| 2005/0152733 A1 | 7/2005 | Patel |
| 2006/0165829 A1 | 7/2006 | Smith et al. |
| 2006/0283447 A1 | 12/2006 | Dhuper et al. |
| 2007/0047733 A1 | 3/2007 | Bremer et al. |
| 2007/0051368 A1 | 3/2007 | Seakins et al. |
| 2007/0079982 A1 | 4/2007 | Laurent et al. |
| 2007/0107737 A1 | 5/2007 | Landis et al. |
| 2007/0277828 A1 | 12/2007 | Ho et al. |
| 2008/0078259 A1 | 4/2008 | Duff |
| 2008/0105257 A1 | 5/2008 | Klasek et al. |
| 2008/0105258 A1 | 5/2008 | Deane et al. |
| 2008/0173305 A1 | 7/2008 | Frater |
| 2008/0202512 A1 | 8/2008 | Kressierer et al. |
| 2008/0251073 A1 | 10/2008 | Jassell et al. |
| 2008/0264413 A1 | 10/2008 | Doherty et al. |
| 2009/0078259 A1 | 3/2009 | Kooij et al. |
| 2009/0078440 A1 | 3/2009 | Carlson et al. |
| 2009/0107493 A1 | 4/2009 | Liu et al. |
| 2009/0107496 A1 | 4/2009 | McGhin et al. |
| 2009/0110379 A1 | 4/2009 | McGhin et al. |
| 2009/0126817 A1 | 5/2009 | Gray |
| 2009/0149696 A1 | 6/2009 | Chilton, III |
| 2009/0320840 A1 | 12/2009 | Klasek et al. |
| 2010/0083965 A1 | 4/2010 | Virr et al. |
| 2010/0116272 A1 | 5/2010 | Row et al. |
| 2010/0224276 A1 | 9/2010 | Forrester et al. |
| 2011/0023874 A1 | 2/2011 | Bath et al. |
| 2011/0046494 A1 | 2/2011 | Balji et al. |
| 2011/0155132 A1 | 6/2011 | Virr et al. |
| 2011/0168287 A1 | 7/2011 | Carlson |
| 2012/0125333 A1 | 5/2012 | Bedford |
| 2012/0255758 A1 | 10/2012 | Lee |
| 2013/0104888 A1 | 5/2013 | Landis et al. |
| 2013/0104901 A1 | 5/2013 | Landis et al. |
| 2013/0174839 A1 | 7/2013 | Ging et al. |
| 2013/0239966 A1 | 9/2013 | Klasek et al. |
| 2013/0255677 A1 | 10/2013 | Varga |
| 2013/0280055 A1 | 10/2013 | Daly et al. |
| 2013/0340752 A1 | 12/2013 | Landis et al. |
| 2014/0037276 A1 | 2/2014 | Carlson |
| 2014/0130802 A1 | 5/2014 | Virr et al. |
| 2014/0202460 A1 | 7/2014 | Bath et al. |
| 2014/0216459 A1 | 8/2014 | Vos et al. |
| 2014/0236083 A1 | 8/2014 | Sims |
| 2014/0246021 A1 | 9/2014 | Buechi et al. |
| 2014/0311487 A1 | 10/2014 | Buechi et al. |
| 2014/0318536 A1 | 10/2014 | Landis et al. |
| 2014/0366876 A1 | 12/2014 | Huby et al. |
| 2015/0090260 A1 | 4/2015 | Seakins et al. |
| 2015/0108670 A1 | 4/2015 | Magee |
| 2015/0306333 A1 | 10/2015 | Amadio et al. |
| 2016/0008560 A1 | 1/2016 | Kwok |
| 2016/0256657 A1 | 9/2016 | Klasek et al. |
| 2016/0271356 A1 | 9/2016 | Robertson et al. |
| 2016/0354573 A1 | 12/2016 | Buswell et al. |
| 2017/0095637 A1 | 4/2017 | Seakins |
| 2017/0100556 A1 | 4/2017 | Munkelt et al. |
| 2018/0214657 A1 | 8/2018 | Forrester |
| 2018/0214659 A1 | 8/2018 | Forrester |
| 2018/0280651 A1 | 10/2018 | Liu et al. |
| 2019/0001091 A1 | 1/2019 | Bath et al. |
| 2019/0076620 A1 | 3/2019 | Stoks et al. |
| 2020/0016361 A1 | 1/2020 | Buswell et al. |
| 2021/0260330 A1 | 8/2021 | Liu et al. |

FOREIGN PATENT DOCUMENTS

| | | |
|---|---|---|
| AU | 756477 | 6/2000 |
| AU | 780911 | 1/2002 |
| AU | 2003278649 A1 | 6/2004 |
| AU | 2007317198 | 5/2008 |
| AU | 2008237548 | 5/2009 |
| AU | 2008237550 | 5/2009 |
| CA | 2674249 C | 4/2014 |

(56) References Cited

FOREIGN PATENT DOCUMENTS

| | | |
|---|---|---|
| CN | 2243015 Y | 12/1996 |
| CN | 1549910 | 11/2004 |
| CN | 2926729 Y | 7/2007 |
| CN | 101018582 A | 8/2007 |
| CN | 101541367 A | 9/2007 |
| CN | 201672170 U | 12/2010 |
| DE | 36 29 353 | 1/1988 |
| DE | 4020522 A1 | 1/1992 |
| DE | 40 34 611 | 5/1992 |
| DE | 4102223 A1 | 7/1992 |
| DE | 9200567 U1 | 7/1992 |
| DE | 33 11 811 | 10/1994 |
| DE | 94 09 231.1 | 12/1994 |
| DE | 19647548 | 5/1998 |
| DE | 19958296 | 9/2001 |
| DE | 20202906 U1 | 5/2002 |
| DE | 10312881 | 5/2004 |
| DE | 20 2004 006 484 | 9/2005 |
| DE | 202005008152 | 10/2006 |
| DE | 202005008156 | 11/2006 |
| DE | 202006007397 U1 | 9/2007 |
| DE | 102006056781 A1 | 6/2008 |
| DE | 102007003454 | 7/2008 |
| DE | 102007003455 | 8/2008 |
| DE | 202007018764 U1 | 6/2009 |
| DE | 102011055439 A1 | 5/2013 |
| EP | 0111248 A2 | 6/1984 |
| EP | 0201985 | 11/1986 |
| EP | 0232864 A2 | 8/1987 |
| EP | 0 258 928 | 9/1988 |
| EP | 0342802 | 11/1989 |
| EP | 0 481 459 | 4/1992 |
| EP | 0 556 561 | 8/1993 |
| EP | 616 166 | 9/1994 |
| EP | 0621050 A2 | 10/1994 |
| EP | 0672430 A2 | 9/1995 |
| EP | 0 885 623 | 12/1998 |
| EP | 0956068 | 11/1999 |
| EP | 1078645 | 2/2001 |
| EP | 1127583 | 8/2001 |
| EP | 1 138 341 | 10/2001 |
| EP | 1145678 | 10/2001 |
| EP | 1147004 B1 | 2/2003 |
| EP | 1352670 A1 | 10/2003 |
| EP | 1380276 A1 | 1/2004 |
| EP | 1396277 A2 | 3/2004 |
| EP | 1535722 A2 | 6/2005 |
| EP | 1579984 A2 | 9/2005 |
| EP | 1741462 B1 | 11/2007 |
| EP | 2055336 | 5/2009 |
| EP | 2055338 | 5/2009 |
| EP | 2055339 | 5/2009 |
| EP | 2055340 | 5/2009 |
| EP | 2075026 A1 | 7/2009 |
| EP | 2079505 | 7/2009 |
| EP | 2269680 A1 | 1/2011 |
| EP | 2133611 B1 | 9/2011 |
| EP | 2269680 | 9/2012 |
| EP | 2514478 | 7/2013 |
| EP | 2689174 | 1/2014 |
| EP | 2337604 | 3/2014 |
| EP | 2747816 B1 | 1/2018 |
| GB | 1 167 551 | 10/1969 |
| GB | 2056611 | 3/1981 |
| GB | 2173274 | 2/1989 |
| GB | 2 277 689 | 11/1994 |
| JP | S56-109189 U | 8/1981 |
| JP | S59-113392 | 6/1984 |
| JP | 05-317428 | 12/1993 |
| JP | 08-061731 | 3/1996 |
| JP | H08-109984 A | 4/1996 |
| JP | H09-234247 | 9/1997 |
| JP | H09-276408 | 10/1997 |
| JP | H11-033119 A | 2/1999 |
| JP | H11-286058 A | 10/1999 |
| JP | 2001-129091 | 5/2001 |
| JP | 2001-511507 A | 8/2001 |
| JP | 2003-139276 A | 5/2003 |
| JP | 2004-148817 | 5/2004 |
| JP | 44-022293 B2 | 2/2010 |
| NZ | 579384 | 5/2011 |
| NZ | 587113 | 12/2011 |
| NZ | 589766 | 5/2012 |
| NZ | 575837 | 7/2012 |
| NZ | 583968 | 10/2012 |
| NZ | 597827 | 6/2013 |
| NZ | 590924 | 8/2013 |
| NZ | 600986 | 8/2013 |
| NZ | 597179 | 9/2013 |
| NZ | 605324 | 6/2014 |
| NZ | 605326 | 7/2014 |
| NZ | 607629 | 7/2014 |
| NZ | 610299 | 11/2014 |
| NZ | 701541 | 5/2015 |
| NZ | 625795 | 6/2015 |
| NZ | 620739 | 8/2015 |
| NZ | 625605. | 4/2016 |
| NZ | 710351 | 1/2017 |
| NZ | 631008 | 7/2017 |
| SU | 379270 | 4/1973 |
| WO | WO 92/21163 A1 | 11/1992 |
| WO | WO 1996/020748 A1 | 7/1996 |
| WO | WO 97/18001 A1 | 5/1997 |
| WO | WO 98/26826 | 6/1998 |
| WO | WO 01/10489 | 2/2001 |
| WO | WO 02/32486 | 4/2002 |
| WO | WO 2003/022342 | 3/2003 |
| WO | WO 2003/026721 A2 | 4/2003 |
| WO | WO 2004/024429 A1 | 3/2004 |
| WO | WO 2004/039444 A1 | 5/2004 |
| WO | WO 2004/105847 | 12/2004 |
| WO | WO 2004/105848 | 12/2004 |
| WO | WO 2005/021076 | 3/2005 |
| WO | WO 2006/092001 A1 | 9/2006 |
| WO | WO 2006/095151 | 9/2006 |
| WO | WO 2007/051230 A1 | 5/2007 |
| WO | WO 2008/055307 A1 | 5/2008 |
| WO | WO 2008/055308 A1 | 5/2008 |
| WO | WO 2008/060046 A1 | 5/2008 |
| WO | WO 2008/060295 | 5/2008 |
| WO | WO 2008/076230 | 6/2008 |
| WO | WO 2009/015410 A1 | 2/2009 |
| WO | WO 2009/022004 | 2/2009 |
| WO | WO 2010/084183 A2 | 7/2010 |
| WO | WO 2011/051837 A1 | 5/2011 |
| WO | WO 2011/051870 | 5/2011 |
| WO | WO 2011/136665 A1 | 11/2011 |
| WO | WO 2011/162622 A1 | 12/2011 |
| WO | WO 2012/053910 A1 | 4/2012 |
| WO | WO 2012/164407 A1 | 12/2012 |
| WO | WO 2013/026901 A1 | 2/2013 |
| WO | WO 2013/045575 | 4/2013 |
| WO | WO 2013/127474 | 9/2013 |
| WO | WO 2013/137753 | 9/2013 |
| WO | WO 2013/147623 A1 | 10/2013 |
| WO | WO 2013/165263 A1 | 11/2013 |
| WO | WO 2014/025266 | 2/2014 |
| WO | WO 2014/077706 | 5/2014 |
| WO | WO 2014/088430 A1 | 6/2014 |
| WO | WO 2014/205513 | 12/2014 |
| WO | WO 2015/038013 A1 | 3/2015 |
| WO | WO 2015/142192 | 9/2015 |
| WO | WO 2017/043981 A1 | 3/2017 |
| WO | WO 2018/116187 | 6/2018 |

OTHER PUBLICATIONS

Supplementary Search Report in corresponding European Patent Application No. 17883717.5, dated Jun. 19, 2020, in 3 pages.
International Preliminary Report on Patentability in corresponding International Patent Application No. PCT/IB2017/058182, dated Feb. 13, 2018, in 9 pages.

(56) References Cited

OTHER PUBLICATIONS

International Search Report and Written Opinion for PCT/IB2017/058182 dated Feb. 13, 2018 in 19 pages.
MR810 Respiratory Humidifier Technical Manual, Revision C.
Fisher & Paykel Healthcare, Annual Report 2003.
Fisher & Paykel Healthcare, FY04 Full Year Overview & Update, May 24, 2004.
Fisher & Paykel Healthcare, Full Year Analyst Briefing, Jun. 5, 2002.
MR850 Respiratory Humidifier Instruction Sheet, Rev. G, Feb. 2004.
Fisher & Paykel Healthcare, 900HC506 Heated Wall Tube Part Brochure, Jul. 10, 2001, in 1 page.
Fisher & Paykel Healthcare, 900HC506/505 Product Specification, Jul. 10, 2001, in 3 pages.

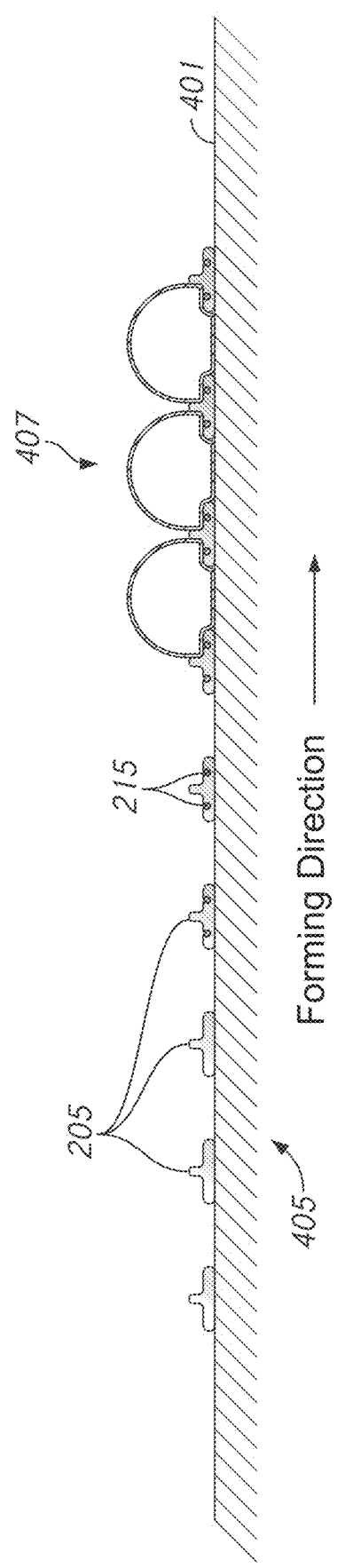

MEDICAL TUBES AND METHODS OF MANUFACTURE

FIELD OF THE DISCLOSURE

This disclosure relates generally to tubes suitable for medical use, and in particular to tubes for use in medical circuits suitable for providing gases to and/or removing gases from a patient, such as in positive airway pressure (PAP), respirator, anaesthesia, ventilator, and insufflation systems and having heating wires and sensor wires extending through the tube.

BACKGROUND

In medical circuits, various components transport warm and/or humidified gases to and from patients. For example, in some breathing circuits such as PAP or assisted breathing circuits, gases inhaled by a patient are delivered from a heater-humidifier through an inspiratory tube. As another example, tubes can deliver humidified gas (commonly $CO_2$) into the abdominal cavity in insufflation circuits. This can help prevent "drying out" of the patient's internal organs, and can decrease the amount of time needed for recovery from surgery. Unheated tubing allows significant heat loss to ambient cooling. This cooling may result in unwanted condensation or "rainout" along the length of the tubing transporting warm, humidified air.

SUMMARY

The present disclosure discloses tubing that allows for improved temperature and/or humidity control in medical circuits. Medical tubes and methods of manufacturing medical tubes are disclosed herein. The tube can include a plurality of heating wires and at least one sensor wire. Arrangements are disclosed for reducing the effects of noise on the sensor wire caused by the heating wires. The noise can include undesired capacitance effects between the heating wires and the sensor wire that result in inaccurate sensor measurements. The arrangements can include placing each of at least two heating wires an equal distance from the sensor wire to effectively cancel the capacitance effect. The arrangements can include providing an additional offsetting physical capacitance in the tube arrangement. Other possible arrangements are further disclosed herein to correct for potential inaccuracies.

Although the present disclosure is described mainly with respect to a spirally wound tube structure, it is to be understood that the presently disclosed filament arrangement between heating wires and sensor wires is not limited to the particular tubes disclosed herein, but extends to any tube structures which include heating wires and sensor wires.

A tube for conveying humidified gases to a patient can comprise first and second heating wires traversing at least a portion of the length of the tube; and a sensor wire in electrical communication with a temperature sensor, wherein the first and second heating wires and the sensor wire can be arranged in close proximity within the tube and the first and second heating wires are spaced equal distance from the sensor wire. The first and second heating wires and the sensor wire can be all located along a line on a longitudinal cross-sectional plane of the tube. The first and second heating wires and the sensor wire can be located along a line substantially parallel to a longitudinal axis of the tube in the longitudinal cross-sectional plane of the tube. The first heating wire can be located on a first side of the sensor wire and the second heating wire can be located on a second side of the sensor wire. The tube can further comprise a ground wire. The first and second heating wires can be spaced equal distance from both the sensor wire and the ground wire. The sensor wire can be between the first and second heating wires, and the ground wire can be on an opposite side of the first or second heating wire as the sensor wire. The sensor wire and the ground wire can be between the first and second sensor heating wires. The sensor wire and the ground wire can be arranged substantially vertically in the longitudinal cross-sectional plane of the tube.

A tube for conveying humidified gases to a patient can comprise first and second heating wires traversing at least a portion of the length of the tube; a sensor wire in electrical communication with a temperature sensor; and a capacitor coupled between one of the first and second heater wires, and the sensor wire, wherein at least one of the first and second heating wires and the sensor wire can be arranged in close proximity within the tube and the capacitor is configured to correct for capacitive coupling between the at least one of the first and second heating wires and the sensor wire. The first and second heating wires and the sensor wire can be all located along a line on a longitudinal cross-sectional plane of the tube. The first heating wire can be located on a first side of the sensor wire and the second heating wire can be located on a second side of the sensor wire. A distance between the first heating wire and the sensor wire can be smaller than a distance between the second heating wire and the sensor wire. The capacitor can be coupled between the second heater wire and the sensor wire. The tube can further comprise a ground wire. The sensor wire can be between the first and second heating wires, and the ground wire can be on an opposite side of the first or second heating wire as the sensor wire. The sensor wire and the ground wire can be between the first and second heating wires. The sensor wire and the ground wire can be arranged substantially vertically in the longitudinal cross-sectional plane of the tube.

The foregoing tubes can have one, some, or all of the following properties, as well as properties described elsewhere in this disclosure. The tube can have a length of greater than 1.5 meters. The tube can have a length of greater than 1.6 meters. The tube can have a length of greater than 1.7 meters. The tube can have a length of greater than 1.8 meters. The tube can have a length of greater than 2 meters.

The foregoing tubes can have one, some, or all of the following properties, as well as properties described elsewhere in this disclosure. The foregoing tubes may be a composite structure made of two or more distinct components that are spirally wound to form an elongate tube. One of the components may be a spirally wound elongate hollow body, and the other component may be an elongate structural component also spirally wound between turns of the spirally wound hollow body. The foregoing tubes need not be made from distinct components. An elongate hollow body formed (for example, extruded) from a single material may be spirally wound to form an elongate tube. The elongate hollow body itself may, in transverse cross-section, have a thin wall portion and a relatively thicker or more rigid reinforcement portion. The tubes can be incorporated into a variety of medical circuits or may be employed for other medical uses.

The foregoing tubes can have one, some, or all of the following properties, as well as properties described elsewhere in this disclosure. The foregoing tubes can be a composite tube comprising a first elongate member comprising a hollow body spirally wound to form at least in part an elongate tube having a longitudinal axis, a lumen extending along the longitudinal axis, and a hollow wall surrounding the lumen. A second elongate member may be spirally wound and joined between adjacent turns of the first elongate member, the second elongate member forming at least a portion of the lumen of the elongate tube. The name "first elongate member" and "second elongate member" do not necessarily connote an order, such as the order in which the components are assembled. As described herein, the first elongate member and the second elongate member can also be portions of a single tube-shaped element.

The foregoing tubes can have one, some, or all of the following properties, as well as properties described elsewhere in this disclosure.

The first elongate member can be a tube. The first elongate member can form, in longitudinal cross-section, a plurality of bubbles. A portion of surfaces of the plurality of bubbles can form the lumen. The bubbles can have a flattened surface at the lumen. Adjacent bubbles can be separated by a gap above the second elongate member, or may not be directly connected to each other. The plurality of bubbles can be adjacent one another without stacking. The plurality of bubbles can be adjacent one another and stacked. The bubbles can have perforations. The second elongate member can have a longitudinal cross-section that is wider proximal the lumen and narrower at a radial distance from the lumen. The second elongate member can have a longitudinal cross-section that is generally triangular, generally T-shaped, or generally Y-shaped. One or more conductive filaments can be embedded or encapsulated in the second elongate member. The one or more conductive filaments can be heating filaments (such as resistance heating filaments) and/or sensing filaments. The one or more conductive filaments embedded or encapsulated in the second elongate member can be one or more of the first heater wire, the second heater wire, the sensor wire, and/or the ground wire. The tube can comprise pairs of conductive filaments, such as two or four conductive filaments. Pairs of conductive filaments can be formed into a connecting loop at one end of the composite tube. The one or more conductive filaments can be spaced from the lumen wall. The second elongate member can have a longitudinal cross-section that is generally triangular, generally T-shaped, or generally Y-shaped, and one or more conductive filaments, such as the one or more of the first heater wire, the second heater wire, the sensor wire, and/or the ground wire can be embedded or encapsulated in the second elongate member on opposite sides of the triangle, T-shape, or Y-shape. The filaments can have specific arrangements to reduce capacitive noise between the filaments as described above. Alternatively, physical capacitors can be included in the tube arrangement to offset capacitive effects as described above. Further, software can be included in a medical device connected to the tube for adjusting measurements due to known capacitive effects.

The foregoing tubes can be incorporated into a medical circuit component, an inspiratory tube, an expiratory tube, a PAP component, an insufflation circuit, an exploratory component, or a surgical component, among other applications.

The foregoing tubes can be manufactured by the following method of manufacturing a composite tube. The resulting tube can have one, some, or all of the properties described above or anywhere in this disclosure. The method can comprise providing a first elongate member comprising a hollow body and a second elongate member configured to provide structural support for the first elongate member. The second elongate member can be spirally wrapped around a mandrel with opposite side edge portions of the second elongate member being spaced apart on adjacent wraps, thereby forming a second-elongate-member spiral. The first elongate member can be spirally wrapped around the second-elongate-member spiral, such that portions of the first elongate member overlap adjacent wraps of the second-elongate-member spiral and a portion of the first elongate member can be disposed adjacent the mandrel in the space between the wraps of the second-elongate-member spiral, thereby forming a first-elongate-member spiral.

The foregoing method can comprise one, some, or all of the following. The method can comprise supplying air at a pressure greater than atmospheric pressure to an end of the first elongate member. The method can comprise cooling the second-elongate-member spiral and the first-elongate-member spiral, thereby forming a composite tube having a lumen extending along a longitudinal axis and a hollow space surrounding the lumen. The method can comprise forming the first elongate member. The method can comprise extruding the first elongate member with a first extruder. The method can comprise forming the second elongate member. The method can comprise extruding the second elongate member with a second extruder. The second extruder can be configured to encapsulate one or more conductive filaments in the second elongate member. Forming the second elongate member can comprise embedding conductive filaments in the second elongate member. The conductive filaments can be non-reactive with the second elongate member. The conductive filaments can comprise alloys of aluminum or copper or other conductive materials. The method can comprise forming pairs of conductive filaments into a connecting loop at one end of the composite tube. The first extruder can be distinct from the second extruder.

The foregoing tubes can have one, some, or all of the following properties, as well as properties described elsewhere in this disclosure. The tube can comprise an elongate hollow body spirally wound to form an elongate tube having a longitudinal axis, a lumen extending along the longitudinal axis, and a hollow wall surrounding the lumen, wherein the elongate hollow body can have, in transverse cross-section, a wall defining at least a portion of the hollow body. The tube can further comprise a reinforcement portion extending along a length of the elongate hollow body being spirally positioned between adjacent turns of the elongate hollow body, wherein the reinforcement portion can form a portion of the lumen of the elongate tube. The reinforcement portion can be relatively thicker or more rigid than the wall of the elongate hollow body.

The foregoing tube can have one, some, or all of the following properties, as well as properties described elsewhere in this disclosure. The reinforcement portion can be formed from the same piece of material as the elongate hollow body. The elongate hollow body in transverse cross-section can comprise two reinforcement portions on opposite sides of the elongate hollow body, wherein spiral winding of the elongate hollow body can join adjacent reinforcement portions to each other such that opposite edges of the reinforcement portions can touch on adjacent turns of the elongate hollow body. Opposite side edges of the reinforcement portions can overlap on adjacent turns of the elongate hollow body. The reinforcement portion can be made of a separate piece of material than the elongate hollow body. The hollow body can form in longitudinal cross-section a plurality of bubbles. A portion of surfaces of the plurality of bubbles can form the lumen. The bubbles can have a flattened surface at the lumen. The bubbles can have perforations. The medical tube can also comprise one or more conductive filaments embedded or encapsulated within the reinforcement portion. The conductive filament can be a heating filament and/or or sensing filament, such as one or more of the first heater wire, the second heater wire, the sensor wire, and/or the ground wire. The medical tube can comprise two conductive filaments, wherein one conductive filament is embedded or encapsulated in each of the reinforcement portions. The medical tube can comprise two or more conductive filaments positioned on only one side of the elongate hollow body. Pairs of conductive filaments can be formed into a connecting loop at one end of the elongate tube. The one or more filaments can be spaced from the lumen wall.

The foregoing tube can be incorporated into a medical circuit component, an inspiratory tube, an expiratory tube, a PAP component, an insufflation circuit, an exploratory component, or a surgical component, among other applications.

The foregoing tubes can be manufactured by the following method of manufacturing a medical tube. The method can comprise spirally winding an elongate hollow body around a mandrel to form an elongate tube having a longitudinal axis, a lumen extending along the longitudinal axis, and a hollow wall surrounding the lumen, wherein the elongate hollow body can have, in transverse cross-section, a wall defining at least a portion of the hollow body and two reinforcement portions on opposite sides of the elongate body forming a portion of the wall of the lumen, the two reinforcement portions being relatively thicker or more rigid than the wall defining at least a portion of the hollow body. The method can further comprise joining adjacent reinforcement portions to each other such that opposite edges of the reinforcement portions can touch on adjacent turns of the elongate hollow body.

The foregoing method can comprise one, some, or all of the following or any other properties described elsewhere in this disclosure. Joining adjacent reinforcement portions to each other can cause edges of the reinforcement portions to overlap. The method can further comprise supplying air at a pressure greater than atmospheric pressure to an end of the elongate hollow body. The method can further comprise cooling the elongate hollow body to join the adjacent reinforcement portions to each other. The method can further comprise extruding the elongate hollow body. The method can further comprise embedding conductive filaments in the reinforcement portions. The method can further comprise forming pairs of conductive filaments into a connecting loop at one end of the elongate tube.

A patient gases supply controller configured to determine a temperature of gases supplied to a patient and adjust a one or more heating elements of a gases supply system can comprise a processor configured to receive information about an arrangement of any of the foregoing tubes. The received information can comprise heater and/or sensor wires arrangements of the tube, and/or capacitive effects between the heater and sensor wires. The processor can be further configured to calibrate sensor measurements, and/or change modes and/or operational parameters based at least in part on the received information. The sensor measurements can comprise temperature measurements.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

Example embodiments that implement the various features of the disclosed systems and methods will now be described with reference to the drawings. The drawings and the associated descriptions are provided to illustrate embodiments and not to limit the scope of the disclosure.

FIG. 4F shows another aspect in a method for forming the composite tube.

Throughout the drawings, reference numbers are re-used to indicate correspondence between referenced (or similar) elements. In addition, the first digit of each reference number indicates the figure in which the element first appears.

DETAILED DESCRIPTION

Details regarding several illustrative embodiments for implementing the apparatuses and methods described herein are described below with reference to the figures. The invention is not limited to these described embodiments.

Breathing Circuit Comprising One or More Medical Tubes

Figure 1:
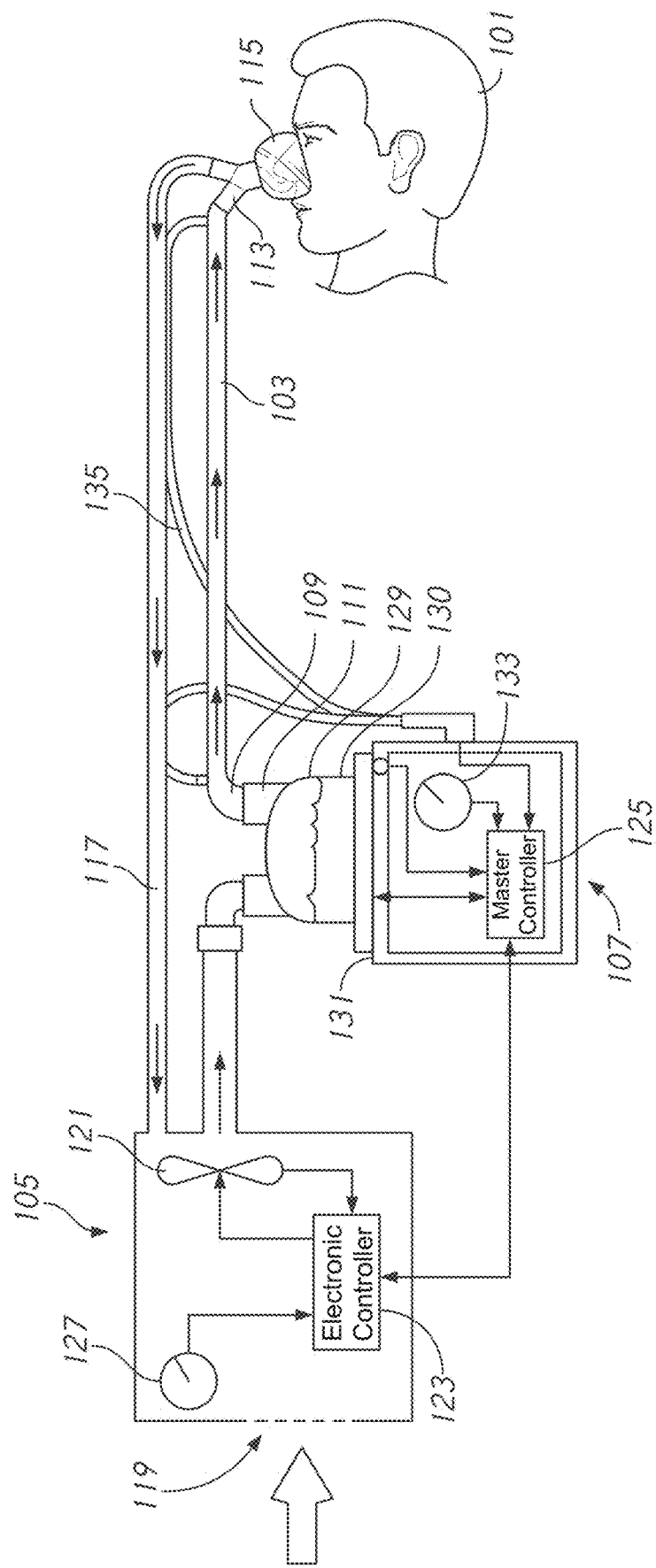
FIG. 1 shows a schematic illustration of a medical circuit incorporating one or more medical tubes.

For a more detailed understanding of the disclosure, reference is first made to FIG. 1, which shows an example respiratory system including one or more medical tubes. Tube is a broad term and is to be given its ordinary and customary meaning to a person of ordinary skill in the art (that is, it is not to be limited to a special or customized meaning) and includes, without limitation, non-cylindrical passageways. A composite tube may generally be defined as a tube comprising two or more portions or components, as described in greater detail below. Such a respiratory system can be a continuous, variable, or bi-level positive airway pressure (PAP) system or other form of respiratory therapy.

Gases can be transported in a gases flow path of FIG. 1 as follows. Dry gases can pass from a flow generator 105, such as a ventilator or blower, to a humidifier 107 via an inlet port. The humidifier 107 can humidify the dry gases. The humidifier 107 can connect to an inlet 109 (the end for receiving humidified gases) of an inspiratory tube 103 via a humidifier outlet port 111, thereby supplying humidified gases to the inspiratory tube 103. An inspiratory tube is a tube that is configured to deliver breathing gases to a patient, and may be made from a composite tube or other tubes as described in further detail below. The gases can flow through the inspiratory tube 103 to an outlet 113 (the end for expelling humidified gases), and then to the patient 101 through a patient interface 115 connected to the outlet 113.

An expiratory tube 117 can also optionally connect to the patient interface 115. An expiratory tube is a tube that is configured to move exhaled humidified gases away from a patient. Here, the expiratory tube 117 can return exhaled humidified gases from the patient interface 115 to the flow generator 105.

The dry gases enter the flow generator 105 through a vent 119. A fan 121 can improve the gases flow into the flow generator by drawing air or other gases through vent 119. The fan 121 can be, for example, a variable speed fan, where an electronic controller 123 can control the fan speed. The function of the electronic controller 123 can be controlled by an electronic master controller 125 in response to inputs from the master controller 125 and/or a user-set predetermined required value (preset value) of pressure and/or fan speed via a dial 127.

The humidifier 107 comprises a humidification chamber 129 containing a volume of water 130 or other suitable humidifying liquid. The humidification chamber 129 can be removable from the humidifier 107 after use. Removability allows the humidification chamber 129 to be more readily sterilized or disposed. However, the humidification chamber 129 portion of the humidifier 107 can be a unitary construction. The body of the humidification chamber 129 can be formed from a non-conductive glass or plastics material. The humidification chamber 129 can also include conductive components. The humidification chamber 129 can include a heat-conductive base (for example, an aluminum base) contacting or associated with a heater plate 131 on the humidifier 107.

The humidifier 107 can also include electronic controls. The humidifier 107 includes an electronic, analog or digital master controller 125. The master controller 125 can be a microprocessor-based controller executing computer software commands stored in associated memory. In response to the user-set humidity and/or temperature value input via a user interface 133, and/or other inputs, the master controller 125 can determine when (or to what level) to energize heater plate 131 to heat the water 130 within humidification chamber 129.

Any suitable patient interface 115 can be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks and nasal masks), cannulas, and nasal pillows. A temperature sensor 135 can connect to the inspiratory tube 103 near the patient interface 115, or to the patient interface 115. The temperature sensor 135 can monitor the temperature near or at the patient interface 115. A heating filament (not shown) associated with the temperature sensor 135 can be used to adjust the temperature of the patient interface 115 and/or inspiratory tube 103 to raise the temperature of the inspiratory tube 103 and/or patient interface 115. The temperature of the patient interface 115 and/or inspiratory tube 103 can be raised above the saturation temperature, thereby reducing the opportunity for condensation, which can be unwanted and/or undesirable.

In FIG. 1, exhaled humidified gases can be returned from the patient interface 115 to the flow generator 105 via an expiratory tube 117. The expiratory tube 117 can also be a composite tube, or other tubes, as described in greater detail below. However, the expiratory tube 117 can also be a medical tube. The expiratory tube 117 can have a temperature sensor and/or heating element, such as a heater wire, as described above with respect to the inspiratory tube 103. The temperature sensor and/or the heating element can be integrated with the expiratory tube 117 to reduce the opportunity for condensation. The expiratory tube 117 need not return exhaled gases to the flow generator 105. Exhaled humidified gases can be passed directly to ambient surroundings or to other ancillary equipment, such as an air scrubber/filter. The expiratory tube can be omitted in some breathing circuits.

Composite Tubes

The medical tube may be a composite structure made of two or more distinct components. The two or more distinct components can be spirally wound to form an elongate tube. One of the components may be a spirally wound elongate hollow body, and the other component may be an elongate structural component also spirally wound between turns of the spirally wound hollow body. The tube also need not be made from distinct components. An elongate hollow body formed (for example, extruded) from a single material may be spirally wound to form an elongate tube. The elongate hollow body itself may, in transverse cross-section, have a thin wall portion and a relatively thicker or more rigid reinforcement portion. The tubes can be incorporated into a variety of medical circuits or may be employed for other medical uses.

A composite tube can comprise a first elongate member comprising a hollow body spirally wound to form at least in part an elongate tube having a longitudinal axis, a lumen extending along the longitudinal axis, and a hollow wall surrounding the lumen. A second elongate member may be spirally wound and joined between adjacent turns of the first elongate member, the second elongate member forming at least a portion of the lumen of the elongate tube. The name "first elongate member" and "second elongate member" do not necessarily connote an order, such as the order in which the components are assembled. As described herein, the first elongate member and the second elongate member can also be portions of a single tube-shaped element.

The composite tube can have one, some, or all of the following properties, as well as properties described elsewhere in this disclosure.

The first elongate member can be a tube. The first elongate member can form, in longitudinal cross-section, a plurality of bubbles with a flattened surface at the lumen. Adjacent bubbles can be separated by a gap above the second elongate member, or may not be directly connected to each other. The bubbles can have perforations. The second elongate member can have a longitudinal cross-section that is wider proximal the lumen and narrower at a radial distance from the lumen. Specifically, the second elongate member can have a longitudinal cross-section that is generally triangular, generally T-shaped, or generally Y-shaped. One or more conductive filaments can be embedded or encapsulated in the second elongate member. The one or more conductive filaments can be heating filaments (or more specifically, resistance heating filaments) and/or sensing filaments. The tube can comprise pairs of conductive filaments, such as two or four conductive filaments. Pairs of conductive filaments can be formed into a connecting loop at one end of the composite tube. The one or more conductive filaments can be spaced from the lumen wall. The second elongate member can have a longitudinal cross-section that is generally triangular, generally T-shaped, or generally Y-shaped, and one or more conductive filaments can be embedded or encapsulated in the second elongate member on opposite sides of the triangle, T-shape, or Y-shape. The filaments can have specific arrangements to reduce capacitive noise between the filaments. Physical capacitors can also be included in the tube arrangement to offset capacitive effects. Further, software can be included in a medical device connected to the tube for adjusting measurements due to known capacitive effects.

The composite tube described herein can be incorporated into a medical circuit component, an inspiratory tube, an expiratory tube, a PAP component, an insufflation circuit, an exploratory component, or a surgical component, among other applications.

Figure 2A:
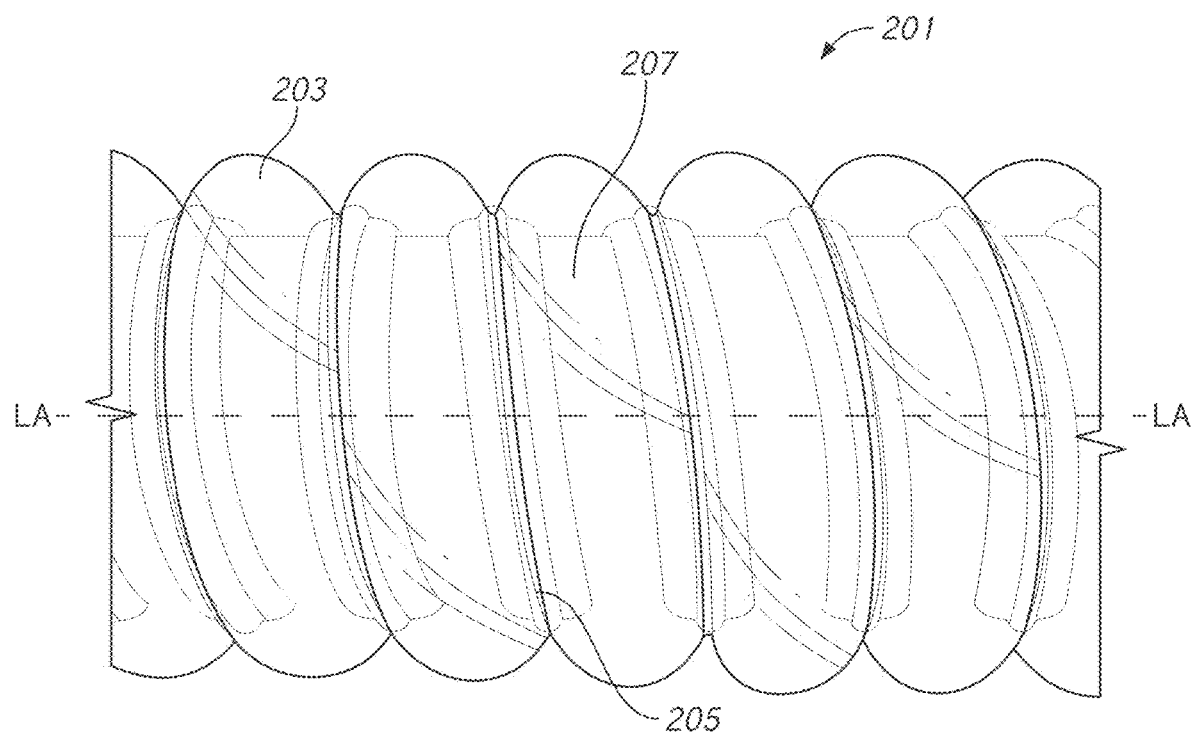
FIG. 2A shows a side-plan view of a section of an example composite tube.

FIG. 2A shows a side-plan view of a section of example composite tube 201. The composite tube 201 can comprise a first elongate member 203 and a second elongate member 205. Member is a broad term and is to be given its ordinary and customary meaning to a person of ordinary skill in the art, which is not to be limited to a special or customized meaning, and includes, without limitation, integral portions, integral components, and distinct components. Thus, although FIG. 2A illustrates an example tube made of two distinct components, the first elongate member 203 and second elongate member 205 can also represent regions in a tube formed from a single material (such as described in FIGS. 5A-5D below). The first elongate member 203 can represent a hollow portion of a tube, while the second elongate member 205 can represent a structural supporting or reinforcement portion of the tube which adds structural support to the hollow portion. The hollow portion and the structural supporting portion can have a spiral configuration, as described herein. The composite tube 201 may be used to form the inspiratory tube 103 and/or the expiratory tube 117 as described above, a coaxial tube as described below, or any other tubes as described elsewhere in this disclosure.

As shown in FIG. 2A, the first elongate member 203 comprises a hollow body spirally wound to form, at least in part, an elongate tube 201 having a longitudinal axis LA-LA. The tube 201 can have a lumen 207 extending along the longitudinal axis LA-LA. The first elongate member 203 can be a hollow tube. The first elongate member 203 can be flexible. The first elongate member 203 can be transparent or, at least, semi-transparent or semi-opaque. A degree of optical transparency allows a caregiver or user to inspect the lumen 207 for blockage and/or contaminants, and/or to confirm the presence of moisture. A variety of plastics, including medical grade plastics, are suitable for the body of the first elongate member 203. Examples of suitable materials include Polyolefin elastomers, Polyether block amides, Thermoplastic co-polyester elastomers, EPDM-Polypropylene mixtures, Thermoplastic polyurethanes, and the like.

The hollow body structure of the first elongate member 203 can contribute to the insulating properties to the composite tube 201. An insulating tube, such as the tube 201, is desirable because, as explained above, it prevents heat loss. This can allow the tube 201 to deliver gas from a humidifier to a patient while maintaining the gas's conditioned state, such as temperature and/or humidity, with minimal energy consumption.

The hollow portion of the first elongate member 203 can be filled with a gas. The gas can be air, which is desirable because of its low thermal conductivity ($2.62 \times 10^{-2}$ W/m·K at 300K) and very low cost. A gas that is more viscous than air may also advantageously be used, as higher viscosity reduces convective heat transfer. Thus, gases such as argon ($17.72 \times 10^{-3}$ W/m·K at 300K), krypton ($9.43 \times 10^{-3}$ W/m·K at 300K), and xenon ($5.65 \times 10^{-3}$ W/m·K at 300K) can increase insulating performance. Each of these gases is non-toxic, chemically inert, fire-inhibiting, and/or commercially available. The hollow portion of the first elongated member 203 can be sealed at both ends of the tube, causing the gas within to be substantially stagnant. The hollow portion can also function as a secondary pneumatic connection, such as a pressure sample line for conveying pressure feedback from the patient-end of the tube 201 to a controller. The first elongate member 203 can be optionally perforated. The surface of the first elongate member 203 can be perforated on an outward-facing surface, opposite the lumen 207. The hollow portion of the first elongate member 203 can also be filled with a liquid. Examples of liquids can include water or other biocompatible liquids with a high thermal capacity. Nanofluids can also be used. An example nanofluid with suitable thermal capacity comprises water and nanoparticles of substances such as aluminum.

The second elongate member 205 can also be spirally wound. The second elongate member 205 can be joined to the first elongate member 203 between adjacent turns of the first elongate member 203. The second elongate member 205 can form at least a portion of the lumen 207 of the elongate tube 201. The second elongate member 205 can act as structural support for the first elongate member 203.

The second elongate member 205 can be wider at the base (proximate the lumen 207) and narrower at the top (radially further away from the lumen 207). For example, the second elongate member can be generally triangular in shape, generally T-shaped, or generally Y-shaped. However, any shape that meets the contours of the corresponding first elongate member 203 is suitable.

The second elongate member 205 can be flexible, to facilitate bending of the tube 201. The second elongate member 205 can be less flexible than the first elongate member 203. This improves the ability of the second elongate member 205 to structurally support the first elongate member 203. The modulus of the second elongate member 205 can be 30-50 MPa (or about 30-50 MPa). The modulus of the first elongate member 203 can be less than the modulus of the second elongate member 205. The second elongate member 205 can be solid or mostly solid. In addition, the second elongate member 205 can encapsulate or house conductive material, such as filaments including but not limited to heating filaments or sensor signal wires. Heating filaments can minimize the cold surfaces onto which condensate from moisture-laden air can form. Heating filaments can also be used to alter the temperature profile of gases in the lumen 207 of composite tube 201.

A variety of polymers and plastics, including medical grade plastics, are suitable for the body of the second elongate member 205. Examples of suitable materials include Polyolefin elastomers, Polyether block amides, Thermoplastic co-polyester elastomers, EPDM-Polypropylene mixtures, Thermoplastic polyurethanes, and the like. The first elongate member 203 and the second elongate member 205 may be made from the same material. The second elongate member 205 may also be made of a different color material from the first elongate member 203, and may be transparent, translucent or opaque. The first elongate member 203 may be made from a clear plastic, and the second elongate member 205 may be made from an opaque blue (or other colored) plastic.

This spirally-wound structure comprising a flexible, hollow body and an integral support can provide crush resistance, while leaving the tube wall flexible enough to permit short-radius bends without kinking, occluding and/or collapsing. The tube can be bent around a 25 mm diameter metal cylinder without kinking, occluding, and/or collapsing, as defined in the test for increase in flow resistance with bending according to ISO 5367:2000(E). This structure also can provide a smooth lumen 207 surface (tube bore), which helps keep the tube free from deposits and improves gases flow. The hollow body has been found to improve the insulating properties of a tube, while allowing the tube to remain light weight.

As explained above, the composite tube 201 can be used as an expiratory tube and/or an inspiratory tube in a breathing circuit, or a portion of a breathing circuit. The composite tube 201 is used at least as an inspiratory tube in some breathing circuits.

Figure 2B:
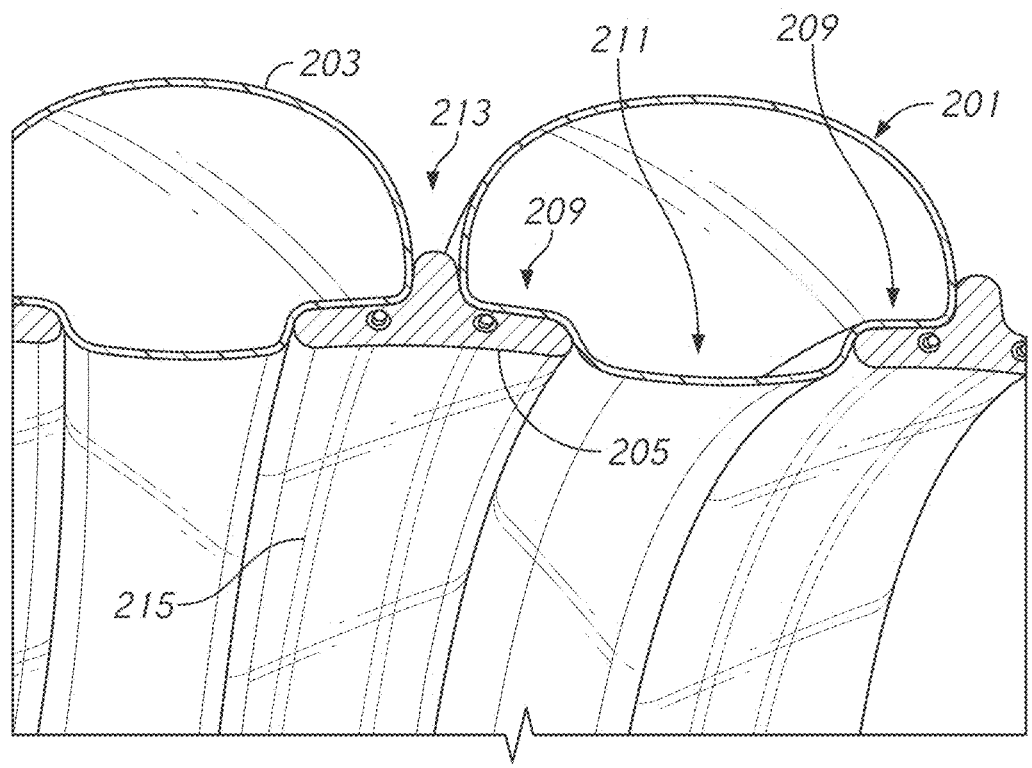
FIG. 2B shows a longitudinal cross-section of a top portion a composite tube.

FIG. 2B shows a longitudinal cross-section of a top portion of the example composite tube 201 of FIG. 2A. FIG. 2B has the same orientation as FIG. 2A. This example further illustrates the hollow-body shape of the first elongate member 203. As seen in this example, the first elongate member 203 forms in longitudinal cross-section a plurality of hollow bubbles. Portions 209 of the first elongate member 203 overlap adjacent wraps of the second elongate member 205. A portion 211 of the first elongate member 203 forms the wall of the lumen (tube bore). A portion of the second elongate member 205 forms the wall of the lumen with the portion 211 of the first elongate member 203.

It was discovered that having a gap 213 between adjacent turns of the first elongate member 203, that is, between adjacent bubbles, unexpectedly improved the overall insulating properties of the composite tube 201. Thus, adjacent bubbles can be separated by a gap 213. Providing a gap 213 between adjacent bubbles can increase the heat transfer resistivity (the R value) and, accordingly, can decrease the heat transfer conductivity of the composite tube 201. This gap configuration can also improve the flexibility of the composite tube 201 by permitting shorter-radius bends. A T-shaped second elongate member 205, as shown in FIG. 2B, can help maintain a gap 213 between adjacent bubbles. Adjacent bubbles can also be touching. For example, adjacent bubbles can be bonded together.

One or more conductive materials can be disposed in the second elongate member 205 for heating or sensing the gases flow. As shown in FIG. 2B, two heating filaments 215 are encapsulated in the second elongate member 205. The two heating filaments 215 can each be on either side of the vertical portion of the "T." The heating filaments 215 comprise conductive material, such as alloys of Aluminum (Al) and/or Copper (Cu), or conductive polymer. The material forming the second elongate member 205 can be selected to be non-reactive with the metal in the heating filaments 215 when the heating filaments 215 reach their operating temperature. The filaments 215 may be spaced away from the lumen 207 so that the filaments 215 are not exposed to the lumen 207. At one end of the composite tube 201, pairs of filaments can be formed into a connecting loop.

A plurality of filaments can be disposed in the second elongate member 205. The filaments can be electrically connected together to share a common rail. For example, a first filament, such as a heating filament, can be disposed on a first side of the second elongate member 205. A second filament, such as a sensing filament, can be disposed on a second side of the second elongate member 205. A third filament, such as a ground filament, can be disposed between the first and second filaments. The first, second, and/or third filaments can be connected together at one end of the second elongate member 205.

Figure 2C:
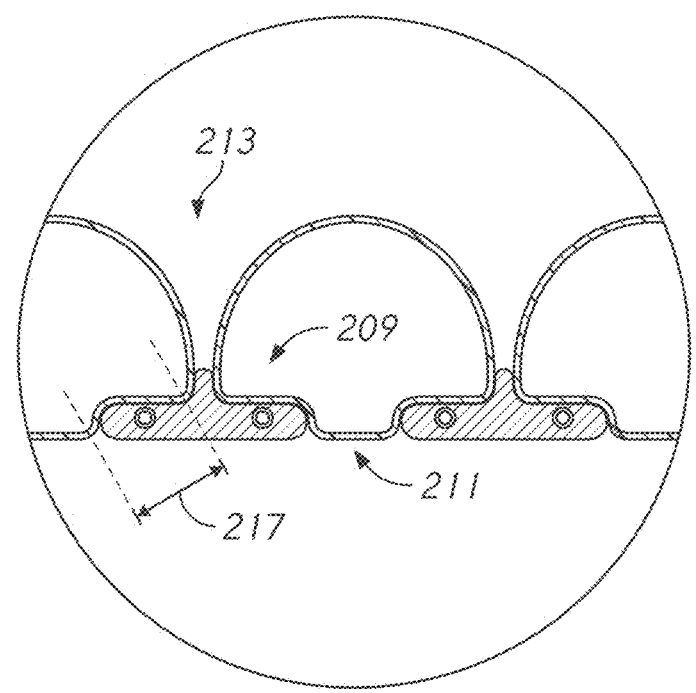
FIG. 2C shows another longitudinal cross-section illustrating a first elongate member in the composite tube.
Figure 2D:
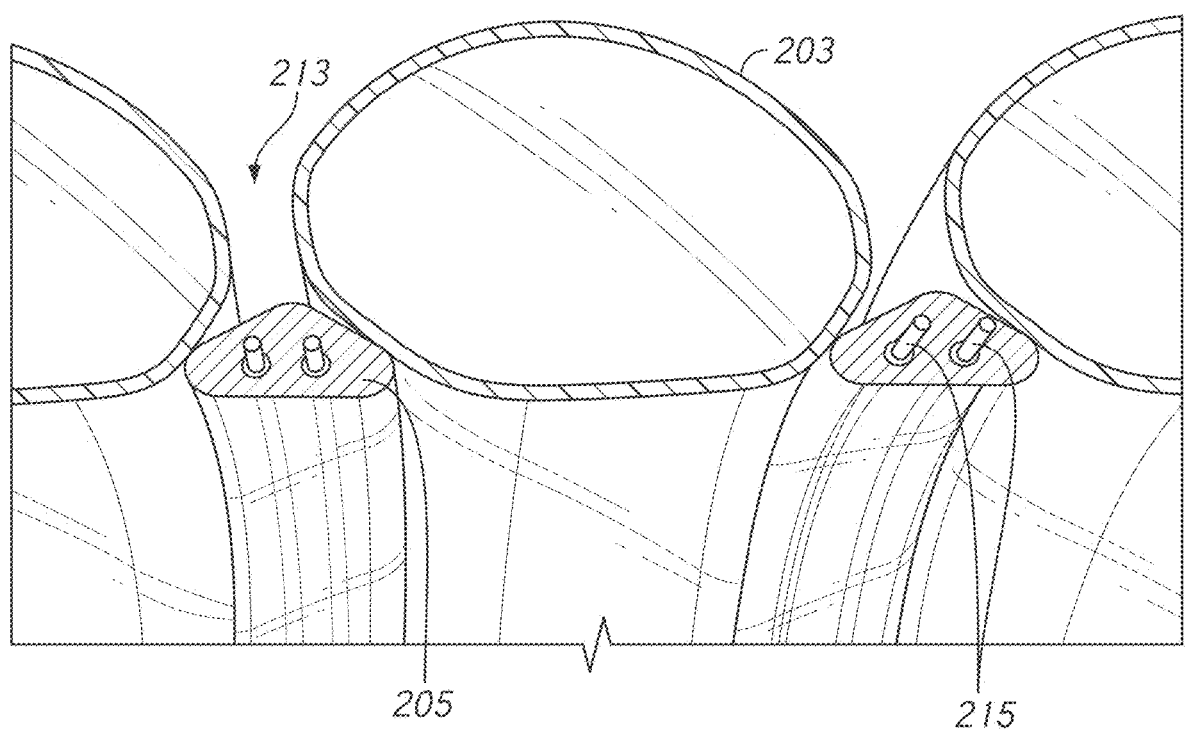
FIG. 2D shows another longitudinal cross-section of a top portion of a composite tube.
Figure 2E:
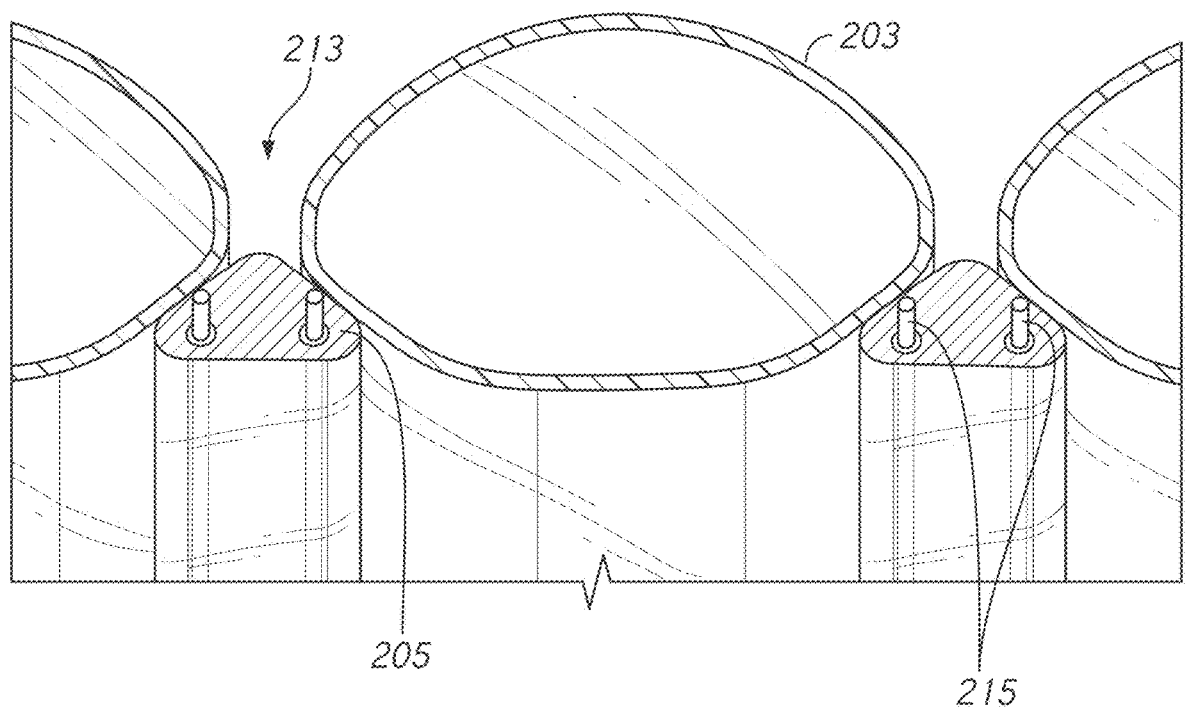
FIG. 2E shows another longitudinal cross-section of a top portion of a composite tube.
Figure 9A:
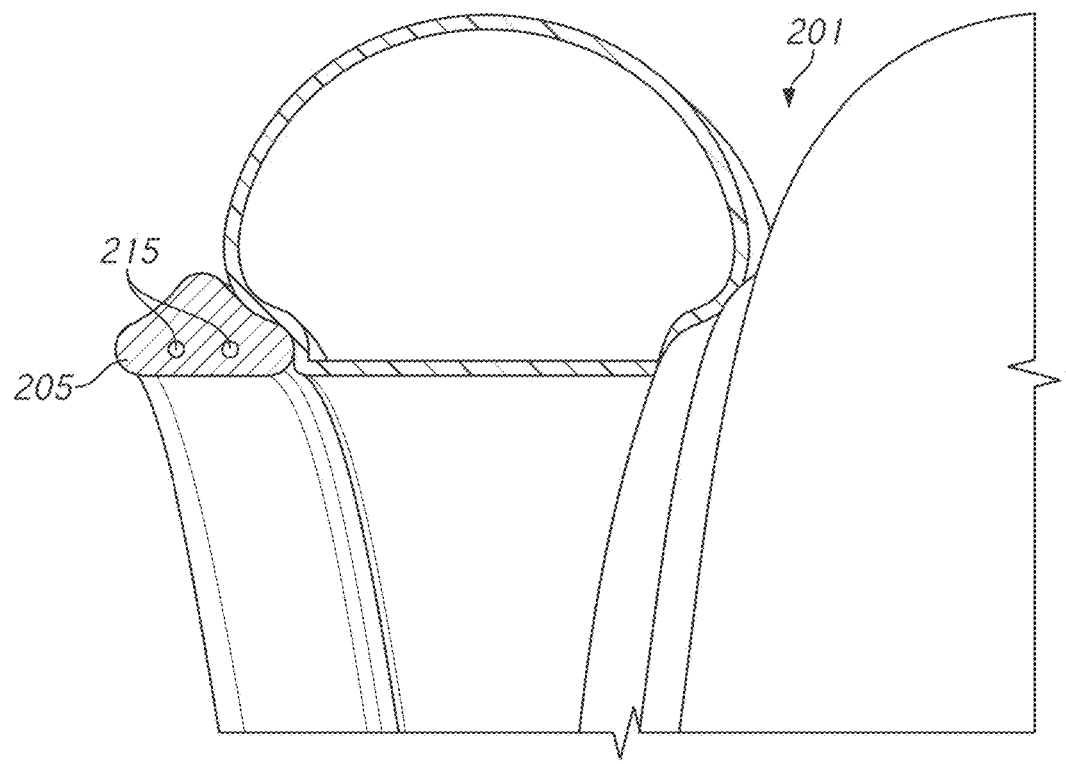
FIGS. 9A-C show examples of first elongate member shapes configured to improve thermal efficiency.
Figure 9B:
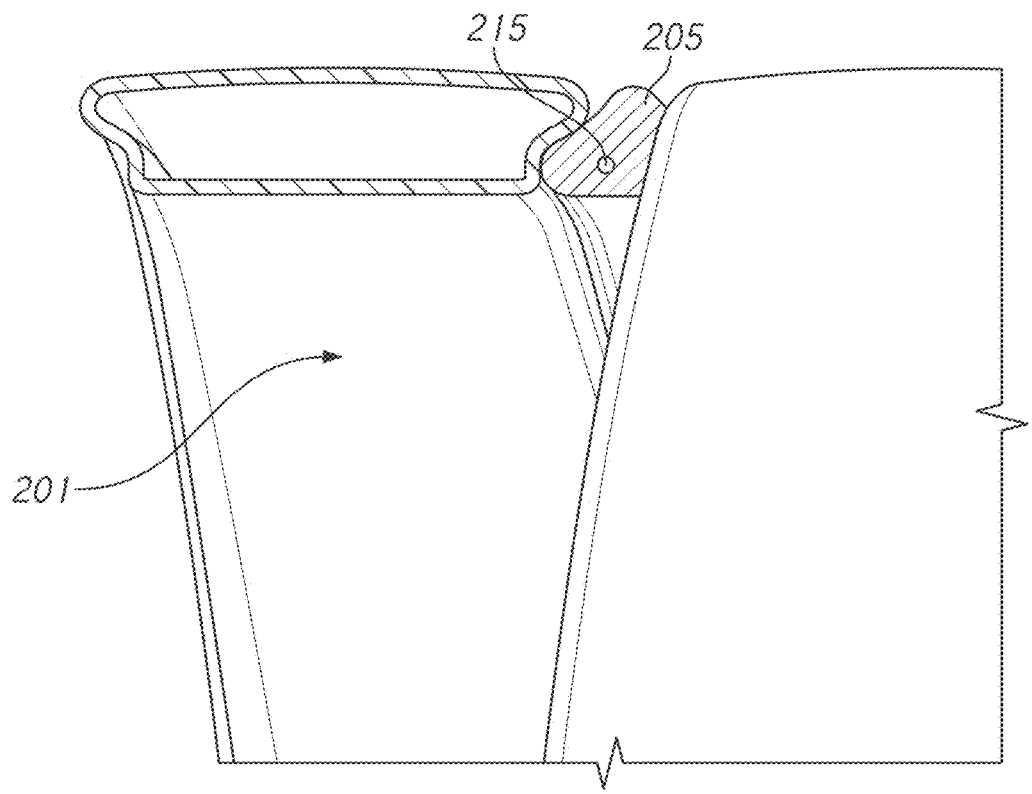
Figure 9C:
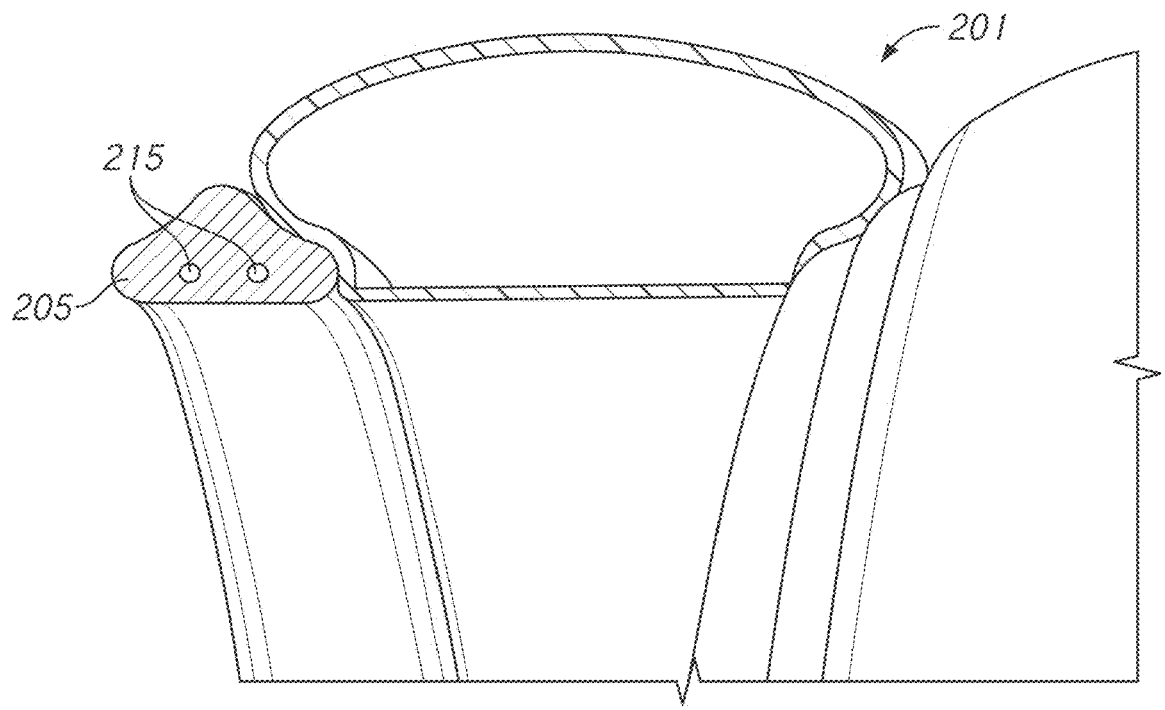

FIG. 2C shows a longitudinal cross-section of the bubbles in FIG. 2B. As shown, the portions 209 of the first elongate member 203 overlapping adjacent wraps of the second elongate member 205 are characterized by a bond region 217. A larger bond region improves the tubes resistance to delamination at the interface of the first and second elongate members. Additionally or alternatively, the shape of the cross section of the second elongate member 205 (hereinafter referred to as a "bead") and/or the bubble can be adapted to increase the bond region 217. For example, FIG. 2D shows a relatively small bonding area on the left-hand side. FIG. 9B also demonstrates a smaller bonding region. In contrast, FIG. 2E shows a larger bonding region than that shown in FIG. 2D, because of the size and shape of the bead. FIGS. 9A and 9C also illustrate a larger bonding region. Each of these figures is discussed in more detail below. It should be appreciated that although the configurations in FIGS. 2E, 9A, and 9C may be utilized, other configurations, including those of FIGS. 2D, 9B, and other variations, may also be utilized as may be desired.

FIG. 2D shows a longitudinal cross-section of a top portion of another composite tube. FIG. 2D has the same orientation as FIG. 2B. This example further illustrates the hollow-body shape of the first elongate member 203 and demonstrates how the first elongate member 203 forms in longitudinal cross-section a plurality of hollow bubbles. In this example, the bubbles are completely separated from each other by a gap 213. A generally triangular second elongate member 205 supports the first elongate member 203.

FIG. 2E shows a longitudinal cross-section of a top portion of another composite tube. FIG. 2E has the same orientation as FIG. 2B. In the example of FIG. 2E, the heating filaments 215 are spaced farther apart from each other than the filaments 215 in FIG. 2B. It was discovered that increasing the space between heating filaments can improve heating efficiency. Heating efficiency refers to the ratio of the amount of heat input to the tube to the amount of energy output or recoverable from the tube. Generally speaking, the greater the energy (or heat) that is dissipated from the tube, the lower the heating efficiency. For improved heating performance, the heating filaments 215 can be equally (or about equally) spaced along the bore of the tube. Alternatively, the filaments 215 can be positioned at extremities of the second elongate member 205, which may provide simpler manufacturing.

Figure 3A:
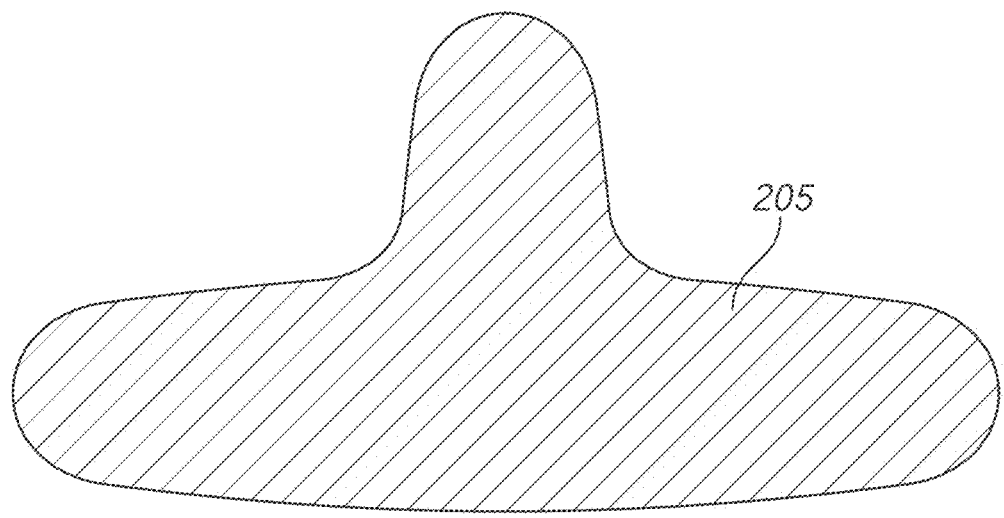
FIG. 3A shows a transverse cross-section of a second elongate member in a composite tube.

Reference is next made to FIGS. 3A through 3G which demonstrate example configurations for the second elongate member 205. FIG. 3A shows a cross-section of a second elongate member 205 having a shape similar to the T-shape shown in FIG. 2B. As shown in FIG. 3A, the second elongate member 205 does not have heating filaments. Other shapes for the second elongate member 205 may also be utilized, including variations of the T-shape as described below and triangular shapes.

Figure 3B:
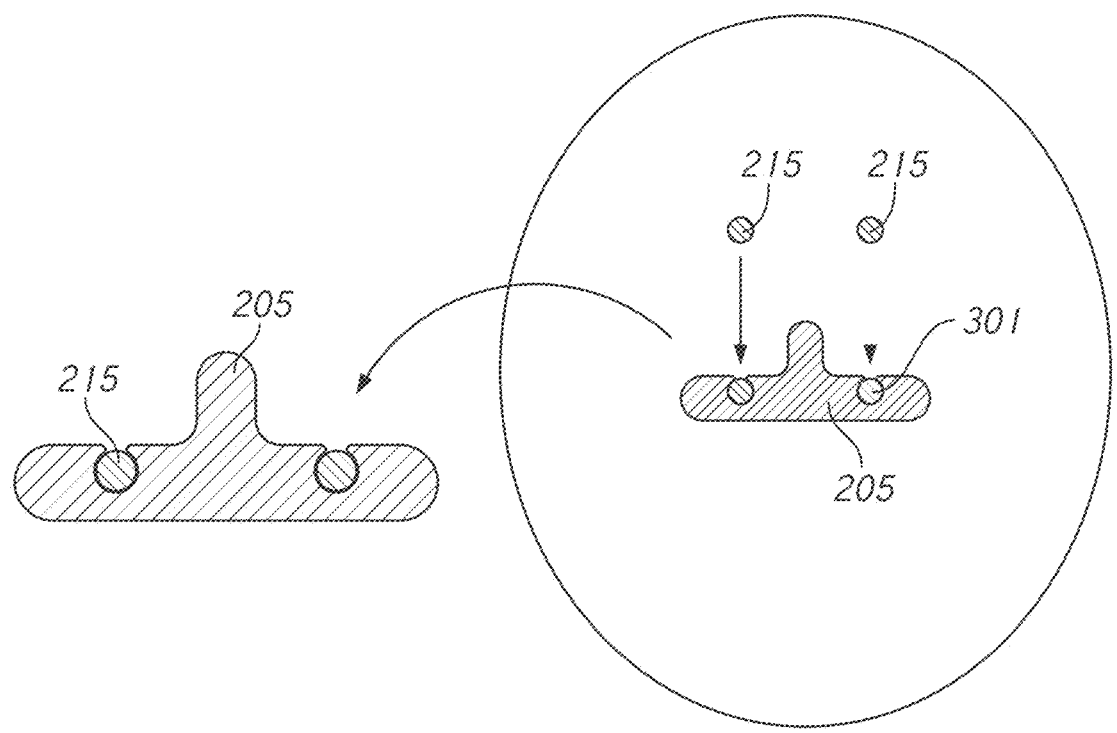
FIG. 3B shows another transverse cross-section of a second elongate member.

FIG. 3B shows another example second elongate member 205 having a T-shape cross-section. In this example, heating filaments 215 are embedded in grooves 301 in the second elongate member 205 on either side of the vertical portion of the "T." The grooves 301 can be formed in the second elongate member 205 during extrusion. The grooves 301 can alternatively be formed in the second elongate member 205 after extrusion. A cutting tool can form the cuts in the second elongate member 205. The grooves 301 can also be formed by the heating filaments 215 as the heating filaments 215 are pressed or pulled (mechanically fixed) into the second elongate member 205 shortly after extrusion, while the second elongate member 205 is relatively soft. Alternatively, one or more heating filaments 215 can be mounted (for example, adhered, bonded, or partially embedded) on the base of the second elongate member 205, such that the filament(s) are exposed to the tube lumen. It can be desirable to contain the exposed filament(s) in insulation to reduce the risk of fire when a flammable gas such as oxygen is passed through the tube lumen.

Figure 3C:
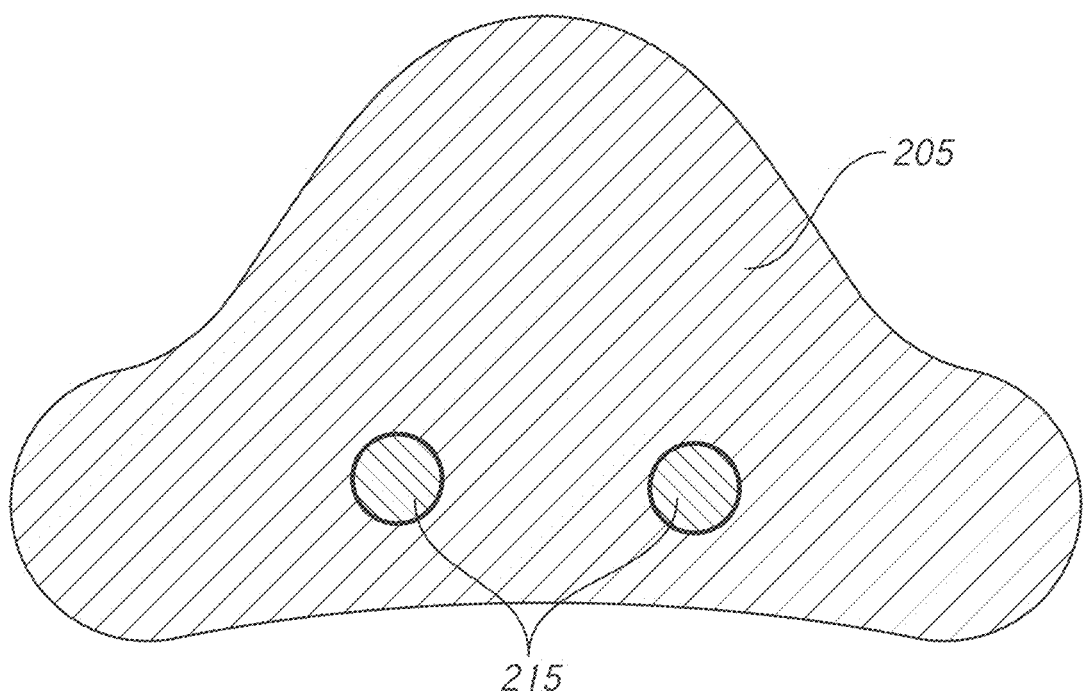
FIG. 3C shows another example second elongate member.

FIG. 3C shows yet another example second elongate member 205 in cross-section. The second elongate member 205 has a generally triangular shape. In this example, heating filaments 215 are embedded on opposite sides of the triangle.

Figure 3D:
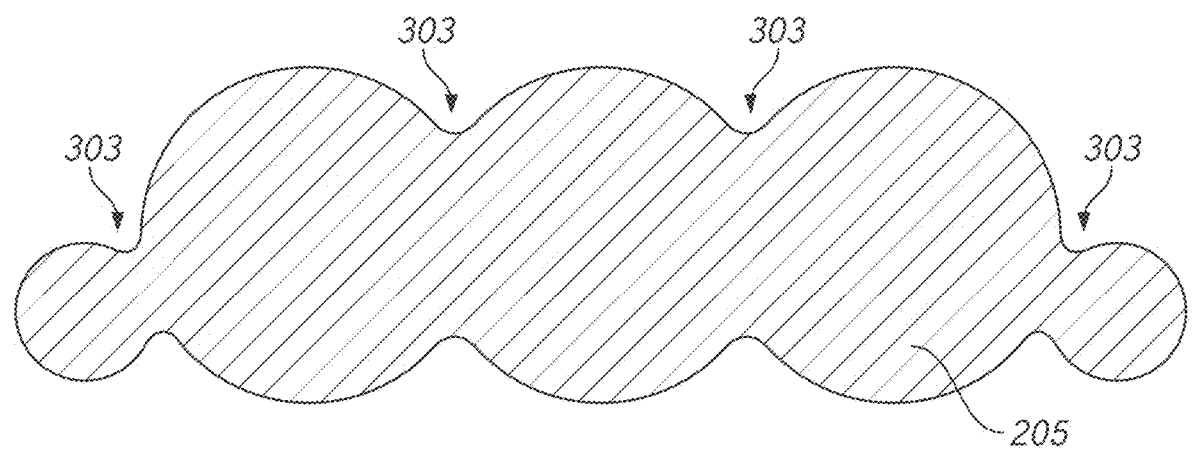
FIG. 3D shows another example second elongate member.

FIG. 3D shows yet another example second elongate member 205 in cross-section. The second elongate member 205 comprises four grooves 303. The grooves 303 are indentations or furrows in the cross-sectional profile. The grooves 303 can facilitate the formation of cuts (not shown) for embedding filaments. The grooves 303 can facilitate the positioning of filaments, which are pressed or pulled into, and thereby embedded in, the second elongate member 205. In this example, the four initiation grooves 303 can facilitate placement of up to four filaments. The four filaments can be four heating filaments, four sensing filaments, two heating filaments and two sensing filaments, three heating filaments and one sensing filament, or one heating filament and three sensing filaments. The heating filaments can also be located on the outside of the second elongate member 205. The sensing filaments can be located on the inside of the second elongate member 205.

Figure 3E:
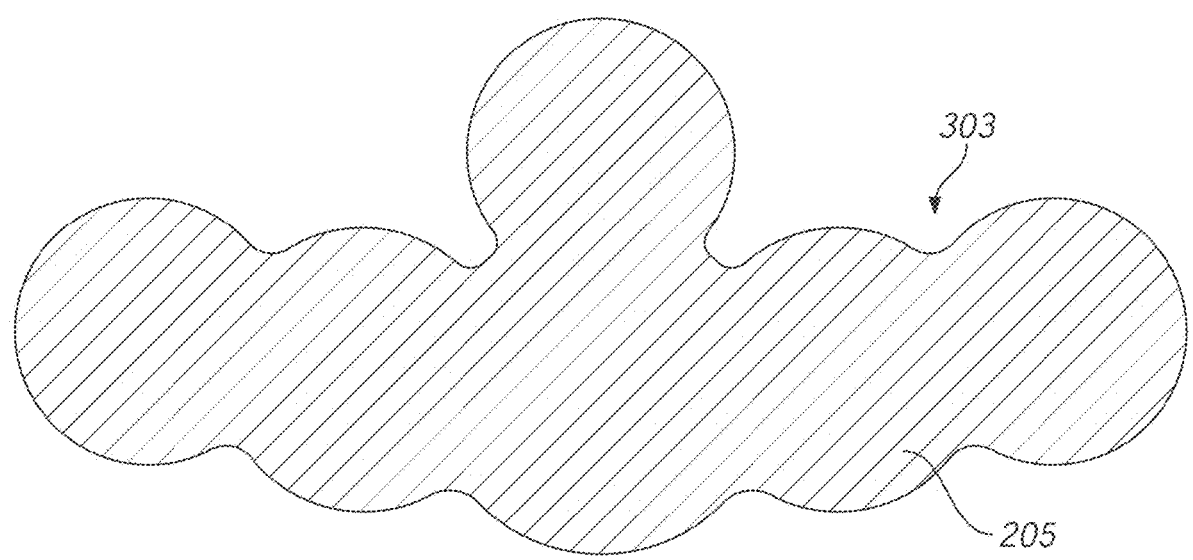
FIG. 3E shows another example second elongate member.

FIG. 3E shows still another example second elongate member 205 in cross-section. The second elongate member 205 has a T-shape profile and a plurality of grooves 303 for placing heating filaments.

Figure 3F:
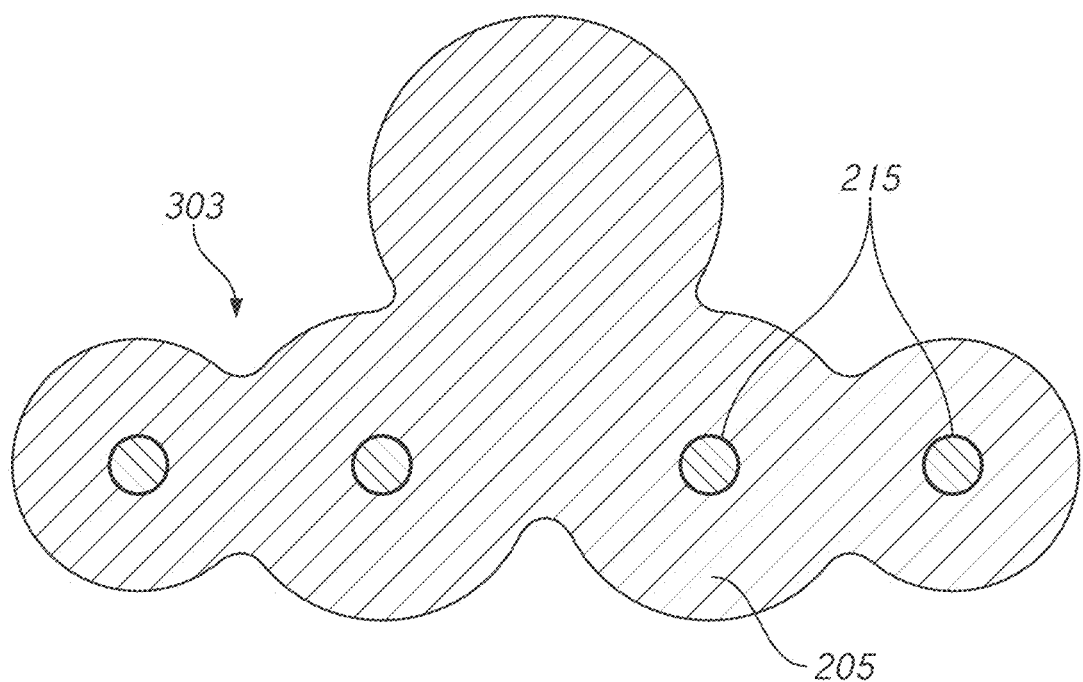
FIG. 3F shows another example second elongate member.

FIG. 3F shows yet another example second elongate member 205 in cross-section. Four filaments 215 are encapsulated in the second elongate member 205, two on either side of the vertical portion of the "T." As explained in more detail below, the filaments 215 can be encapsulated in the second elongate member 205 because the second elongate member 205 was extruded around the filaments. No cuts may be formed to embed the heating filaments 215. As shown in FIG. 3F, the second elongate member 205 also comprises a plurality of grooves 303. Because the heating filaments 215 are encapsulated in the second elongate member 205, the grooves 303 are not used to facilitate formation of cuts for embedding heating filaments. The grooves 303 can facilitate separation of the embedded heating filaments 215, which makes stripping of individual cores easier when, for example, terminating the heating filaments.

Figure 3G:
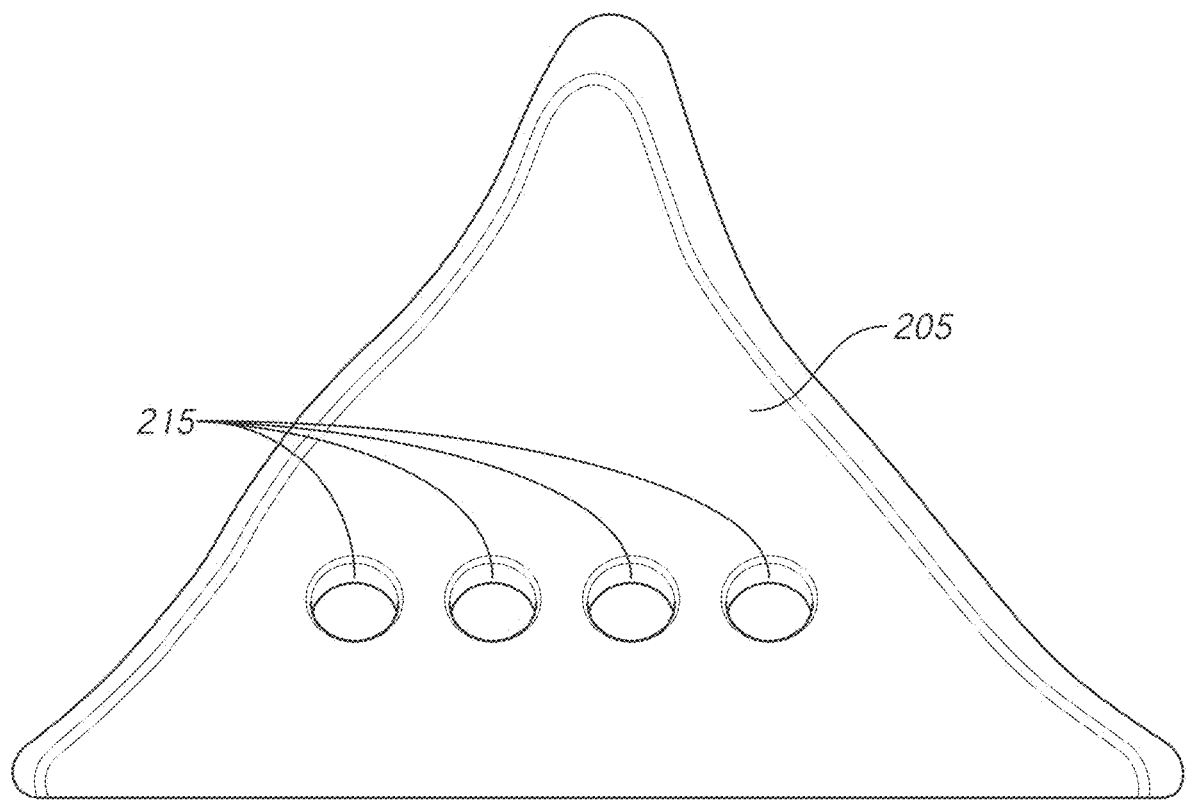
FIG. 3G shows another example second elongate member.

FIG. 3G shows yet another example second elongate member 205 in cross-section. The second elongate member 205 has a generally triangular shape. In this example, the shape of the second elongate member 205 is similar to that of FIG. 3C, but four filaments 215 are encapsulated in the second elongate member 205. All of the filaments 215 can be centrally located in about the bottom third of the second elongate member 205. The filaments 215 can be disposed along a generally horizontal axis.

As explained above, it can be desirable to increase the distance between filaments to improve heating efficiency. However, when heating filaments 215 are incorporated into the composite tube 201, the filaments 215 can also be positioned relatively central in the second elongate member 205. A centralized position promotes robustness of the composite tubing for reuse, due in part to the position reducing the likelihood of the filament breaking upon repeating flexing of the composite tube 201. Centralizing the filaments 215 can also reduce the risk of an ignition hazard because the filaments 215 are coated in layers of insulation and removed from the gases flow path.

As explained above, some of the examples illustrate suitable placements of filaments 215 in the second elongate member 205. In the foregoing examples comprising more than one filament 215, the filaments 215 are generally aligned along a horizontal axis. Alternative configurations are also suitable. For example, two filaments can be aligned along a vertical axis or along a diagonal axis. Four filaments can be aligned along a vertical axis or a diagonal axis. Four filaments can be aligned in a cross-shaped configuration, with one filament disposed at the top of the second elongate member, one filament disposed at the bottom of the second elongate member (near the tube lumen), and two filaments disposed on opposite arms of a "T," "Y," or triangle base.

TABLES 1A and 1B show some example dimensions of medical tubes described herein, as well as some example ranges for these dimensions. The dimensions refer to a transverse cross-section of a tube. In these tables, lumen diameter represents the inner diameter of a tube. Pitch represents the distance between two repeating points measured axially along the tube, namely, the distance between the tip of the vertical portions of adjacent "T"s of the second elongate member. Bubble width represents the width (maximum outer diameter) of a bubble. Bubble height represents the height of a bubble from the tube lumen. Bead height represents the maximum height of the second elongate member from the tube lumen (for example, the height of the vertical portion of the "T"). Bead width represents the maximum width of the second elongate member (for example, the width of the horizontal portion of the "T"). Bubble thickness represents the thickness of the bubble wall.

TABLE 1A

| Feature | Infant Dimension (mm) | Infant Range (±) | Adult Dimension (mm) | Adult Range (±) |
|---|---|---|---|---|
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 2.4 | 1 |
| Bubble height | 2.8 | 1 | 3.5 | 0.5 |
| Bead height | 0.9 | 0.5 | 1.5 | 0.5 |
| Bubble thickness | 0.4 | 0.35 | 0.2 | 0.15 |

TABLE 1B

| Feature | Infant Dimension (mm) | Infant Range (±) | Adult Dimension (mm) | Adult Range (±) |
|---|---|---|---|---|
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 3.4 | 1 |
| Bubble height | 2.8 | 1 | 4.0 | 0.5 |
| Bead height | 0.9 | 0.5 | 1.7 | 0.5 |
| Bubble thickness | 0.4 | 0.35 | 0.2 | 0.15 |

TABLES 2A and 2B provide example ratios between the dimensions of tube features for the tubes described in TABLES 1A and 1B respectively.

TABLE 2A

| Ratios | Infant | Adult |
|---|---|---|
| Lumen diameter:Pitch | 2.3:1 | 2.4:1 |
| Pitch:Bubble width | 1.1:1 | 1.1:1 |
| Pitch:Bead width | 2.2:1 | 3.1:1 |
| Bubble width:Bead width | 2.0:1 | 2.9:1 |
| Lumen diameter:Bubble height | 3.9:1 | 5.1:1 |
| Lumen diameter:Bead height | 12.2:1 | 12.0:1 |
| Bubble height:Bead height | 3.1:1 | 2.3:1 |
| Lumen diameter:Bubble thickness | 27.5:1 | 90.0:1 |

TABLE 2B

| Ratios | Infant | Adult |
|---|---|---|
| Lumen diameter:Pitch | 2.3:1 | 2.4:1 |
| Pitch:Bubble width | 1.1:1 | 1.1:1 |
| Pitch:Bead width | 2.2:1 | 2.2:1 |
| Bubble width:Bead width | 2.0:1 | 2.1:1 |
| Lumen diameter:Bubble height | 3.9:1 | 4.5:1 |
| Lumen diameter:Bead height | 12.2:1 | 10.6:1 |
| Bubble height:Bead height | 3.1:1 | 2.4:1 |
| Lumen diameter:Bubble thickness | 27.5:1 | 90.0:1 |

The following tables show some example properties of a composite tube (labeled "A"), described herein, having a heating filament integrated inside the second elongate member. For comparison, properties of a Fisher & Paykel model RT100 disposable corrugated tube (labeled "B") having a heating filament helically wound inside the bore of the tube are also presented.

Measurement of resistance to flow (RTF) was carried out according to Annex A of ISO 5367:2000(E). The results are summarized in TABLE 3. As seen below, the RTF for the composite tube is lower than the RTF for the model RT100 tube.

TABLE 3

| Flow rate (L/min) | RTF (cm $H_2O$) | | | |
|---|---|---|---|---|
| | 3 | 20 | 40 | 60 |
| A | 0 | 0.05 | 0.18 | 0.38 |
| B | 0 | 0.28 | 0.93 | 1.99 |

Condensate or "rainout" within the tube refers to the weight of condensate collected per day at 20 L/min gases flow rate and room temperature of 18° C. Humidified air is flowed through the tube continuously from a chamber. The tube weights are recorded before and after each day of testing. Three consecutive tests are carried out with the tube being dried in between each test. The results are shown below in TABLE 4. The results showed that rainout is significantly lower in the composite tube than in the model RT100 tube.

TABLE 4

| Tube | A (Day 1) | A (Day 2) | A (Day 3) | B (Day 1) | B (Day 2) | B (day 3) |
|---|---|---|---|---|---|---|
| Weight before (g) | 136.20 | 136.70 | 136.70 | 111.00 | 111.10 | 111.10 |
| Weight after (g) | 139.90 | 140.00 | 139.20 | 190.20 | 178.80 | 167.10 |
| Condensate weight (g) | 3.7 | 3.3 | 2.5 | 79.20 | 67.70 | 56.00 |

The power requirement refers to the power consumed during the condensate test. In this test, the ambient air was held at 18° C. Humidification chambers (see, for example, the humidification chamber 129 in FIG. 1) were powered by MR850 heater bases. The heating filaments in the tubes were powered independently from a DC power supply. Different flow rates were set and the chamber was left to settle to 37° C. at the chamber output. Then, the DC voltage to the circuits was altered to produce a temperature of 40° C. at the circuit output. The voltage required to maintain the output temperature was recorded and the resulting power calculated. The results are shown in TABLE 5. The results show that composite Tube A uses significantly more power than Tube B. This is because Tube B uses a helical heating filament in the tube bore to heat the gas from 37° C. to 40° C. The composite tube does not tend to heat gas quickly because the heating filament is in the wall of the tube (embedded in the second elongate member). Instead, the composite tube is designed to maintain the gas temperature and prevent rainout by maintaining the tube bore at a temperature above the dew point of the humidified gas.

TABLE 5

| Flow rate (L/min) | 40 | 30 | 20 |
| --- | --- | --- | --- |
| Tube A, power required (W) | 46.8 | 38.5 | 37.8 |
| Tube B, power required (W) | 28.0 | 27.5 | 26.8 |

Tube flexibility was tested by using a three-point bend test. Tubes were placed in a three point bend test jig and used along with an Instron 5560 Test System instrument, to measure load and extension. Each tube sample was tested three times; measuring the extension of the tube against the applied load, to obtain average respective stiffness constants. The average stiffness constants for Tube A and Tube B are reproduced in TABLE 6.

TABLE 6

| Tube | Stiffness (N/mm) |
| --- | --- |
| A | 0.028 |
| B | 0.088 |

Methods of Manufacture

A method of manufacturing a composite tube is also disclosed. The resulting tube can have one, some, or all of the properties described above or anywhere in this disclosure. The method can comprise providing a first elongate member including a hollow body and a second elongate member configured to provide structural support for the first elongate member. The second elongate member can be spirally wrapped around a mandrel with opposite side edge portions of the second elongate member being spaced apart on adjacent wraps, thereby forming a second-elongate-member spiral. The first elongate member can be spirally wrapped around the second-elongate-member spiral, such that portions of the first elongate member can overlap adjacent wraps of the second-elongate-member spiral and a portion of the first elongate member can be disposed adjacent the mandrel in the space between the wraps of the second-elongate-member spiral, thereby forming a first-elongate-member spiral.

The foregoing method can also comprise one, some, or all of the following. The method can comprise supplying air at a pressure greater than atmospheric pressure to an end of the first elongate member. The method can comprise cooling the second-elongate-member spiral and the first-elongate-member spiral, thereby forming a composite tube having a lumen extending along a longitudinal axis and a hollow space surrounding the lumen. The method can comprise forming the first elongate member. The method can comprise extruding the first elongate member with a first extruder. The method can comprise forming the second elongate member. The method can comprise extruding the second elongate member with a second extruder. The second extruder can be configured to encapsulate one or more conductive filaments in the second elongate member. Forming the second elongate member can comprise embedding conductive filaments in the second elongate member. The conductive filaments can be non-reactive with the second elongate member. The conductive filaments can comprise alloys of aluminum or copper or other conductive materials. The method can comprise forming pairs of conductive filaments into a connecting loop at one end of the composite tube. The first extruder can be distinct from the second extruder.

Reference is next made to FIGS. 4A through 4F which demonstrate example methods for manufacturing composite tubes.

Figure 4A:
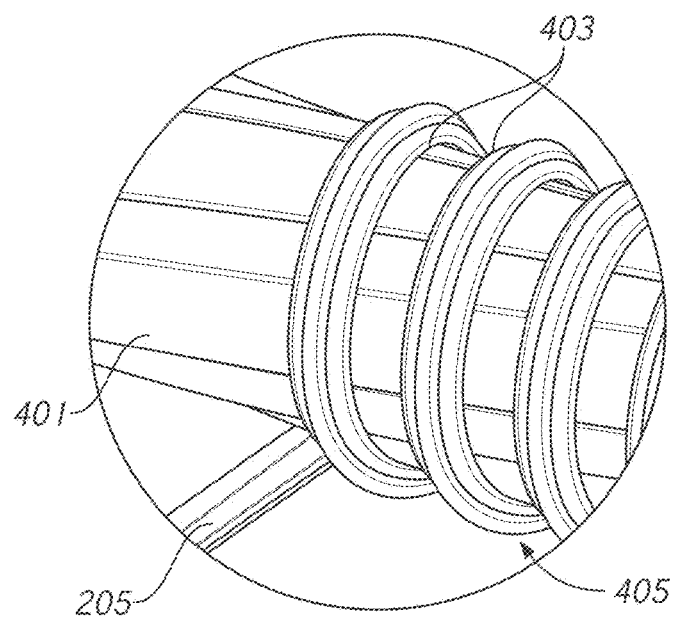
FIG. 4A shows an aspect in a method for forming the composite tube.

Turning first to FIG. 4A, a method of manufacturing a composite tube can comprise providing the second elongate member 205 and spirally wrapping the second elongate member 205 around a mandrel 401 with opposite side edge portions 403 of the second elongate member 205 being spaced apart on adjacent wraps, thereby forming a second-elongate-member spiral 405. The second elongate member 205 may be directly wrapped around the mandrel or around a sacrificial layer provided over the mandrel.

The method can further comprise forming the second elongate member 205. Extrusion can be used for forming the second elongate member 205. The extruder can be configured to extrude the second elongate member 205 with a specified bead height. Thus, the method can comprise extruding the second elongate member 205.

Figure 4B:
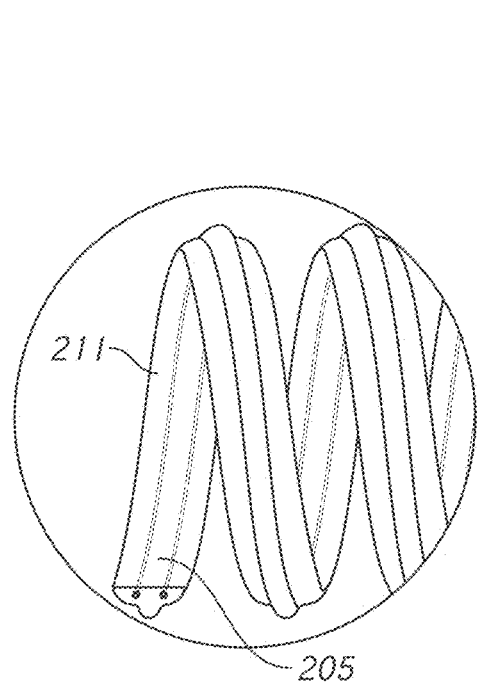
FIG. 4B shows a spiral-wound second elongate member.

As shown in FIG. 4B, extrusion can be advantageous because it can allow heating filaments 215 to be encapsulated in the second elongate member 205 as the second elongate member is formed 205, for example, using an extruder having a cross-head extrusion die. The method can comprise providing one or more heating filaments 215 and encapsulating the heating filaments 215 to form the second elongate member 205. The method can also comprise providing a second elongate member 205 having one or more heating filaments 215 embedded or encapsulated in the second elongate member 205.

Figure 4C:
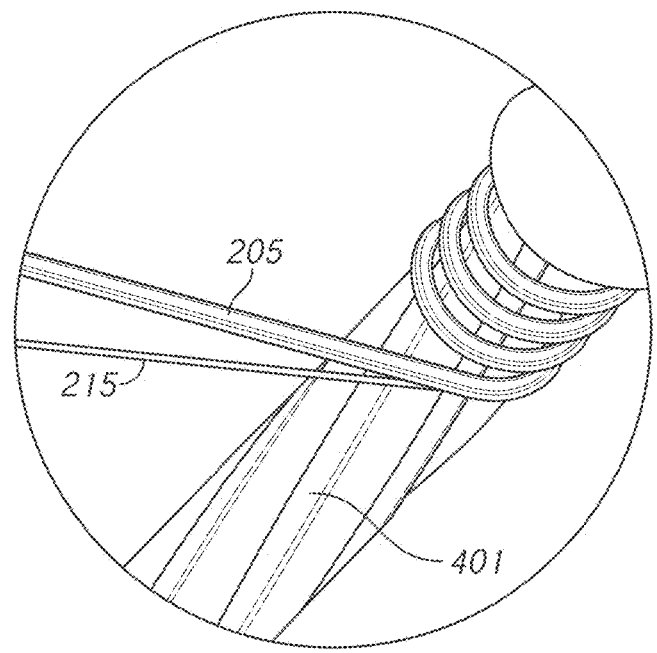
FIG. 4C shows another aspect in a method for forming the composite tube.

The method can comprise embedding one or more filaments 215 in the second elongate member 205. For example, as shown in FIG. 4C, filaments 215 can be pressed (pulled or mechanically positioned) into the second elongate member 205 to a specified depth. Alternatively, cuts can be made in the second elongate member 205 to a specified depth, and the filaments 215 can be placed into the cuts. Pressing or cutting can be done shortly after the second elongate member 205 is extruded and when the second elongate member 205 is soft.

Figure 4D:
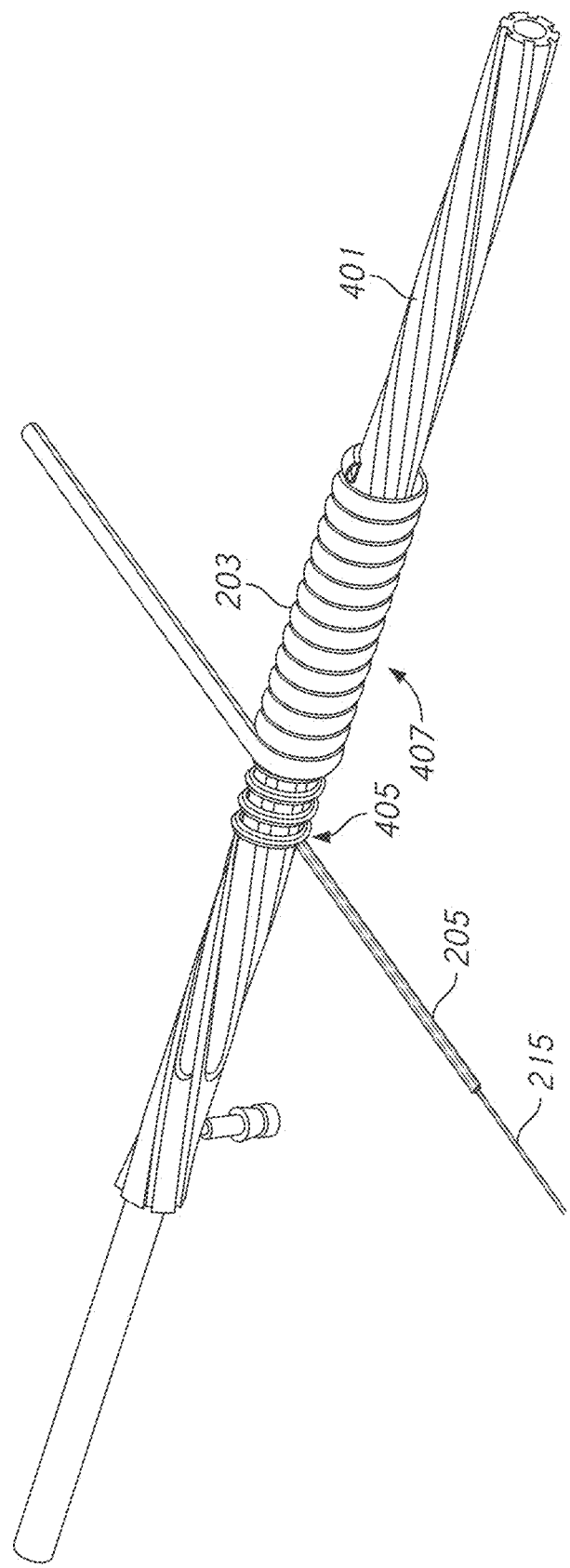
FIG. 4D shows another aspect in a method for forming the composite tube.
Figure 4E:
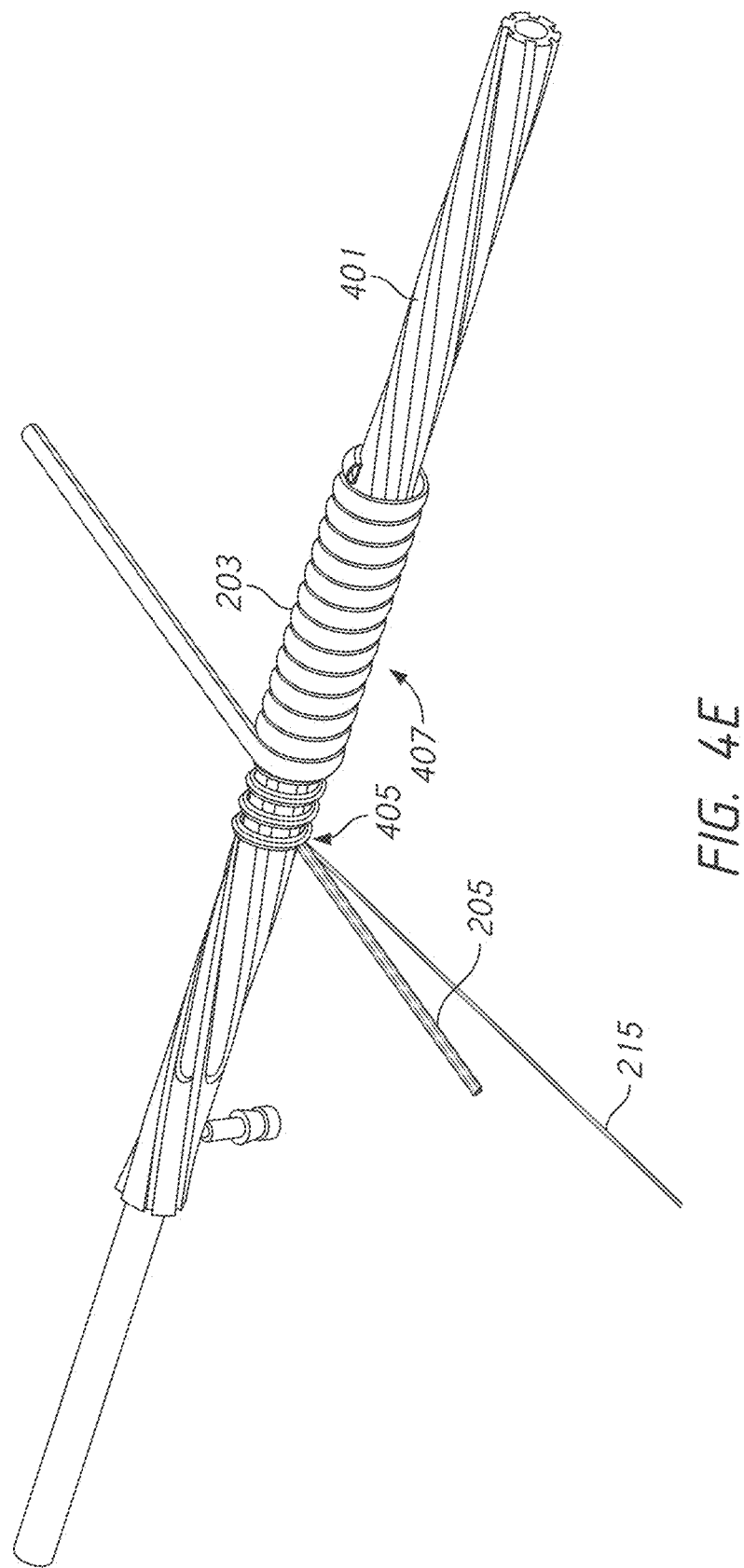
FIG. 4E shows another aspect in a method for forming the composite tube.

As shown in FIGS. 4D and 4E, the method comprises providing the first elongate member 203 and spirally wrapping the first elongate member 203 around the second-elongate-member spiral 405. Portions of the first elongate member 203 can overlap adjacent wraps of the second-elongate-member spiral 405 and a portion of the first elongate member 203 can be disposed adjacent the mandrel 401 in the space between the wraps of the second-elongate-member spiral 405, thereby forming a first-elongate-member spiral 407. FIG. 4D shows such an example method, in which heating filaments 215 are encapsulated in the second elongate member 205, prior to forming the second-elongate-member spiral. FIG. 4E shows such an example method, in which heating filaments 215 are embedded in the second elongate member 205, as the second-elongate-member spiral is formed. An alternative method of incorporating filaments 215 into the composite tube comprises encapsulating one or more filaments 215 between the first elongate member 203 and the second elongate member 205 at a region where the first elongate member 203 overlaps the second elongate member 205.

The above-described alternatives for incorporating one or more heating filaments 215 into a composite tube have advantages over the alternative of having heating filaments in the gases flow path. Having the heating filament(s) 215 out of the gases flow path can improve performance because the filaments heat the tube wall where the condensation is most likely to form. This configuration can also reduce fire risk in high oxygen environments by moving the heating filament out of the gases flow path. Although this feature may reduce the heating wires effectiveness at heating the gases that are passing through the tube, a composite tube 201 can also comprises one or more heating filaments 215 placed within the gases flow path. For example, heating filaments can be emplaced on the lumen wall (tube bore), for example, in a spiral configuration. An example method for disposing one or more heating filaments 215 on the lumen wall can comprise bonding, embedding, or otherwise forming a heating filament on a surface of the second elongate member 205 that, when assembled, forms the lumen wall. Thus, the method can also comprise disposing one or more heating filaments 215 on the lumen wall.

Regardless of whether the heating filaments 215 are embedded or encapsulated on the second elongate member 205 or disposed on the second elongate member 205, or otherwise placed in or on the tube, pairs of filaments can be formed into a connecting loop at one end of the composite tube to form a circuit.

FIG. 4F shows a longitudinal cross-section of the assembly shown in FIG. 4E, focusing on a top portion of the mandrel 401 and a top portion of the first-elongate-member spiral 407 and second-elongate-member spiral 405. This example shows the second-elongate-member spiral 405 having a T-shaped second elongate member 205. As the second-elongate member 205 is formed, heating filaments 215 are embedded in the second elongate member 205. The right side of FIG. 4F shows the bubble-shaped profile of the first-elongate-member spiral 407, as described above.

The method can also comprise forming the first elongate member 203. Extrusion can be used for forming the first elongate member 203. Thus, the method can comprise extruding the first elongate member 203. The first elongate member 203 can also be manufactured by extruding two or more portions and joining them to form a single piece. As another alternative, the first elongate member 203 can also be manufactured by extruding sections that produce a hollow shape when formed or bonded adjacently on a spiral-tube forming process.

The method can also comprise supplying a gas at a pressure greater than atmospheric pressure to an end of the first elongate member 203. The gas can be air, for example. Other gases can also be used, as explained above. Supplying a gas to an end of the first elongate member 203 can help maintain an open, hollow body shape as the first elongate member 203 is wrapped around the mandrel 401. The gas can be supplied before the first elongate member 203 is wrapped around the mandrel 401, while the first elongate member 203 is wrapped around the mandrel 401, or after the first elongate member 203 is wrapped around the mandrel 401. For instance, an extruder with an extrusion die head/tip combination can supply or feed air into the hollow cavity of the first elongate member 203 as the first elongate member 203 is extruded. Thus, the method can comprise extruding the first elongate member 203 and supplying a gas at a pressure greater than atmospheric pressure to an end of the first elongate member 203 after extrusion. A pressure of 15 to 30 cm $H_2O$ (or about 15 to 30 cm $H_2O$) can be used to supply the gas.

The first elongate member 203 and the second elongate member 205 can be spirally wound about the mandrel 401. For example, the first elongate member 203 and second elongate member 205 may come out of an extrusion die at an elevated temperature of 200° C. (or about 200° C.) or more and then be applied to the mandrel after a short distance. The mandrel can be cooled using a water jacket, chiller, and/or other suitable cooling method to a temperature of 20° C. (or about 20° C.) or less, for example, approaching 0° C. (or about 0° C.). After 5 (or about 5) spiral wraps, the first elongate member 203 and second elongate member 205 can be further cooled by a cooling fluid (liquid or gas). The cooling fluid can be air emitted from a ring with jets encircling the mandrel. After cooling and removing the components from the mandrel, a composite tube is formed having a lumen extending along a longitudinal axis and a hollow space surrounding the lumen. No adhesive or other attachment mechanism is needed to connect the first and second elongate members. An adhesive or other attachment mechanism can also be utilized to bond or otherwise connect the two members. The second elongate member 205 after extrusion and placement of the heating filaments may be cooled to freeze the location of the heating filaments. The second elongate member 205 may then be re-heated when applied to the mandrel to improve bonding. Example methods for re-heating include using spot-heating devices, heated rollers, or others.

The method can also comprise formed pairs of heating or sensing filaments into a connecting loop at one end of the composite tube. For example, end sections of two heating or sensing filaments can be extricated from the second elongate member 205 and then formed into a connecting loop, for example, by tying, bonding, adhering, fusing, or otherwise, the two filaments together. As another example, end sections of the heating filaments can be left free from the second elongate member 205 during the manufacturing process and then formed into a connecting loop when the composite tube is assembled.

Medical Tubes and Methods of Manufacture Using a Single Spirally Wound Tube

A medical tube can comprise an elongate hollow body spirally wound to form an elongate tube having a longitudinal axis, a lumen extending along the longitudinal axis, and a hollow wall surrounding the lumen, wherein the elongate hollow body can have in transverse cross-section a wall defining at least a portion of the hollow body. The tube can further comprise a reinforcement portion extending along a length of the elongate hollow body being spirally positioned between adjacent turns of the elongate hollow body, wherein the reinforcement portion can form a portion of the lumen of the elongate tube. The reinforcement portion can be relatively thicker or more rigid than the wall of the elongate hollow body.

The medical tube can also have one, some, or all of the following properties, as well as properties described elsewhere in this disclosure. The reinforcement portion can be formed from the same piece of material as the elongate hollow body. The elongate hollow body in transverse cross-section can comprise two reinforcement portions on opposite sides of the elongate hollow body, wherein spiral winding of the elongate hollow body can join adjacent reinforcement portions to each other such that opposite edges of the reinforcement portions touch on adjacent turns of the elongate hollow body. Opposite side edges of the reinforcement portions can overlap on adjacent turns of the elongate hollow body. The reinforcement portion can be made of a separate piece of material than the elongate hollow body. The hollow body can form in longitudinal cross-section a plurality of bubbles with a flattened surface at the lumen. The bubbles can have perforations. The medical tube can also comprise one or more conductive filaments embedded or encapsulated within the reinforcement portion. The conductive filament can be a heating filament and/or or sensing filament. The medical tube can comprise two conductive filaments, wherein one conductive filament is embedded or encapsulated in each of the reinforcement portions. The medical tube can comprise two or more conductive filaments positioned on only one side of the elongate hollow body. Pairs of conductive filaments can be formed into a connecting loop at one end of the elongate tube. The one or more filaments can be spaced from the lumen wall.

The medical tube described herein can be incorporated into a medical circuit component, an inspiratory tube, an expiratory tube, a PAP component, an insufflation circuit, an exploratory component, or a surgical component, among other applications.

Reference is next made to FIG. 5A through 5F which show transverse cross-sections of tubes comprising a single tube-shaped element having a first elongate member or portion 203 and a reinforcement portion 205A. As illustrated, the reinforcement portions 205A are integral with the first elongate portions 203, and can extend along the entire length of the single tube-shaped element. The single tube-shaped element can be an elongate hollow body having in transverse cross-section a relatively thin wall defining in part the hollow portion 501, with two reinforcement portions 205A with a relatively greater thickness or relatively greater rigidity on opposite sides of the elongate hollow body adjacent the relatively thin wall. These reinforcement portions form a portion of the inner wall of the lumen 207 after the elongate hollow body is spirally wound, such that these reinforcement portions are also spirally positioned between adjacent turns of the elongate hollow body.

The method can comprise forming an elongate hollow body comprising the first elongate portion 203 and the reinforcement portion 205A. Extrusion can be used for forming the elongate hollow body. Example cross-sectional shapes for the tube-shaped element are shown in FIG. 5A through 5F.

The elongate hollow body can be formed into a medical tube, as explained above, and the foregoing discussion is incorporated by this reference.

A method of manufacturing a medical tube can comprise spirally winding an elongate hollow body around a mandrel to form an elongate tube having a longitudinal axis, a lumen extending along the longitudinal axis, and a hollow wall surrounding the lumen, wherein the elongate hollow body can have in transverse cross-section a wall defining at least a portion of the hollow body and two reinforcement portions on opposite sides of the elongate body forming a portion of the wall of the lumen, the two reinforcement portions being relatively thicker or more rigid than the wall defining at least a portion of the hollow body. The method can further comprise joining adjacent reinforcement portions to each other such that opposite edges of the reinforcement portions touch on adjacent turns of the elongate hollow body.

The foregoing method can also comprise one, some, or all of the following or any other properties described elsewhere in this disclosure. Joining adjacent reinforcement portions to each other can cause edges of the reinforcement portions to overlap. The method can further comprise supplying air at a pressure greater than atmospheric pressure to an end of the elongate hollow body. The method can further comprise cooling the elongate hollow body to join the adjacent reinforcement portions to each other. The method can further comprise extruding the elongate hollow body. The method can further comprise embedding conductive filaments in the reinforcement portions. The method can further comprise forming pairs of conductive filaments into a connecting loop at one end of the elongate tube.

Figure 5A:
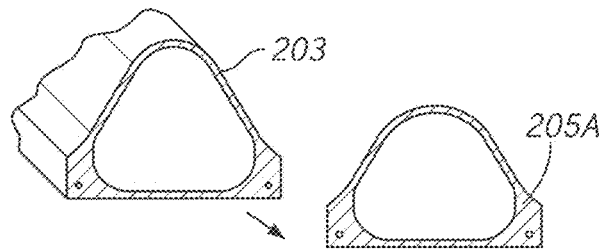
FIGS. 5A-5B shows another example illustrating a single elongate hollow body being spirally wound to form a medical tube.
Figure 5B:
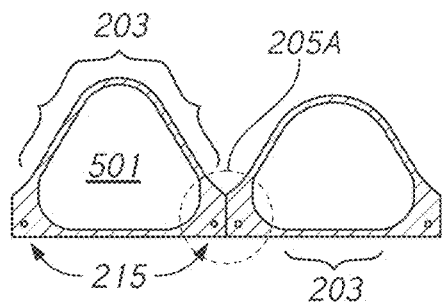
Figure 5C:
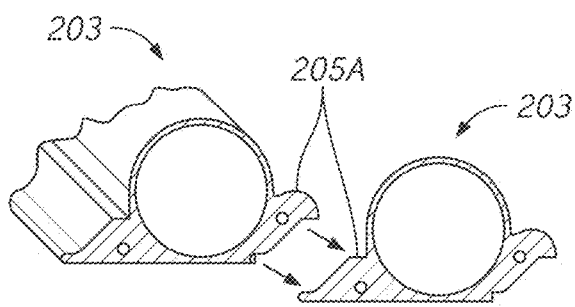
FIGS. 5C-5F shows examples of other single elongate hollow bodies being spirally wound to form a medical tube.
Figure 5D:
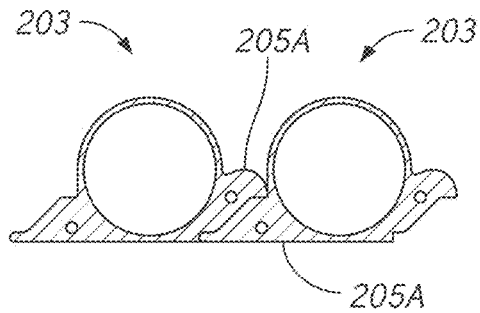
Figures 5E, 5F:
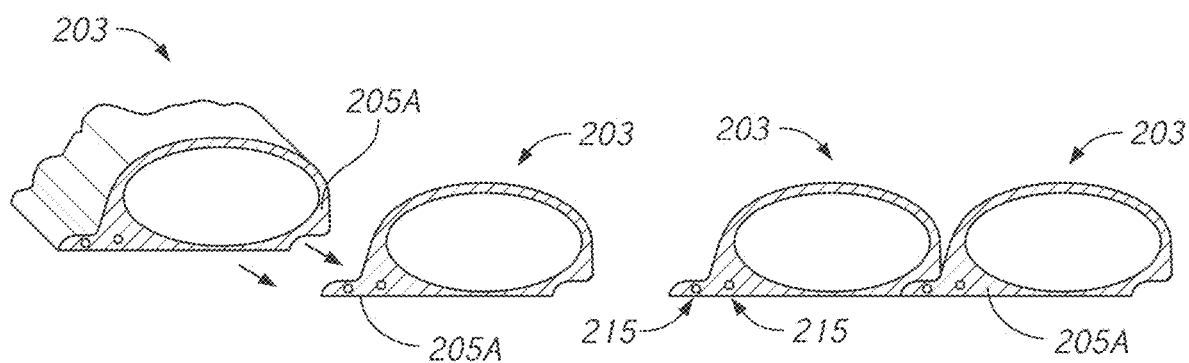

For example, a method of manufacturing a medical tube can comprise spirally wrapping or winding the elongate hollow body around a mandrel. This may be done at an elevated temperature, such that the elongate hollow body is cooled after being spirally wound to join adjacent turns together. As shown in FIG. 5B, opposite side edge portions of the reinforcement portions 205A can touch on adjacent turns. Opposite side edge portions of the reinforcement portions 205A can also overlap on adjacent turns, as shown in FIGS. 5D and 5E. Heating filaments 215 can be incorporated into the reinforcement portions 205A as explained above and as shown in FIG. 5A through 5F. For example, heating filaments may be provided on opposite sides of the elongate hollow portion such as shown in FIGS. 5A-5D. Alternatively, heating filaments may be provided on only one side of the elongate hollow portion, such as shown in FIGS. 5E-5F. Any of these features can also incorporate the presence of sensing filaments.

Medical Circuits

Figure 6:
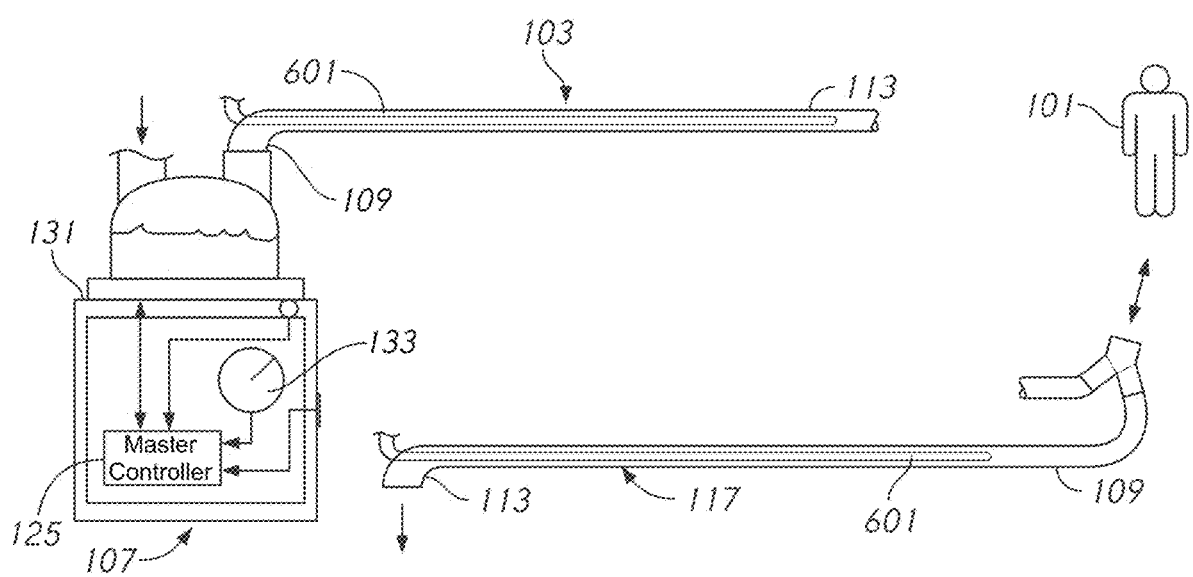
FIG. 6 schematically shows an example medical circuit.

Reference is next made to FIG. 6, which shows an example medical circuit. The circuit comprises one or more composite tubes as described above, namely for the inspiratory tube 103 and/or the expiratory tube 117. The properties of the inspiratory tube 103 and the expiratory tube 117 are similar to the tubes described above with respect to FIG. 1. The inspiratory tube 103 has an inlet 109, communicating with a humidifier 107, and an outlet 113, through which humidified gases are provided to the patient 101. The expiratory tube 117 also has an inlet 109, which receives exhaled humidified gases from the patient 101, and an outlet 113. As described above with respect to FIG. 1, the outlet 113 of the expiratory tube 117 can vent exhaled gases to the atmosphere, to the ventilator/blower unit 107, to an air scrubber/filter, or to any other location.

As described above, heating filaments 601 can be placed within the inspiratory tube 103 and/or the expiratory tube 117 to reduce the risk of rain out in the tubes by maintaining the tube wall temperature above the dew point temperature.

Component of an Insufflation System

Laparoscopic surgery, also called minimally invasive surgery (MIS), or keyhole surgery, is a modern surgical technique. In laparoscopic surgeries, operations in the abdomen are performed through small incisions (usually 0.5 to 1.5 cm) as compared to larger incisions needed in traditional surgical procedures. Laparoscopic surgery includes operations within the abdominal or pelvic cavities. During laparoscopic surgery with insufflation, it may be desirable for the insufflation gas (commonly $CO_2$) to be humidified before being passed into the abdominal cavity. This can help prevent "drying out" of the patient's internal organs, and can decrease the amount of time needed for recovery from surgery. Insufflation systems generally comprise humidifier chambers that hold a quantity of water within them. The humidifier generally includes a heater plate that heats the water to create a water vapour that is transmitted into the incoming gases to humidify the gases. The gases are transported out of the humidifier with the water vapor.

Figure 7:
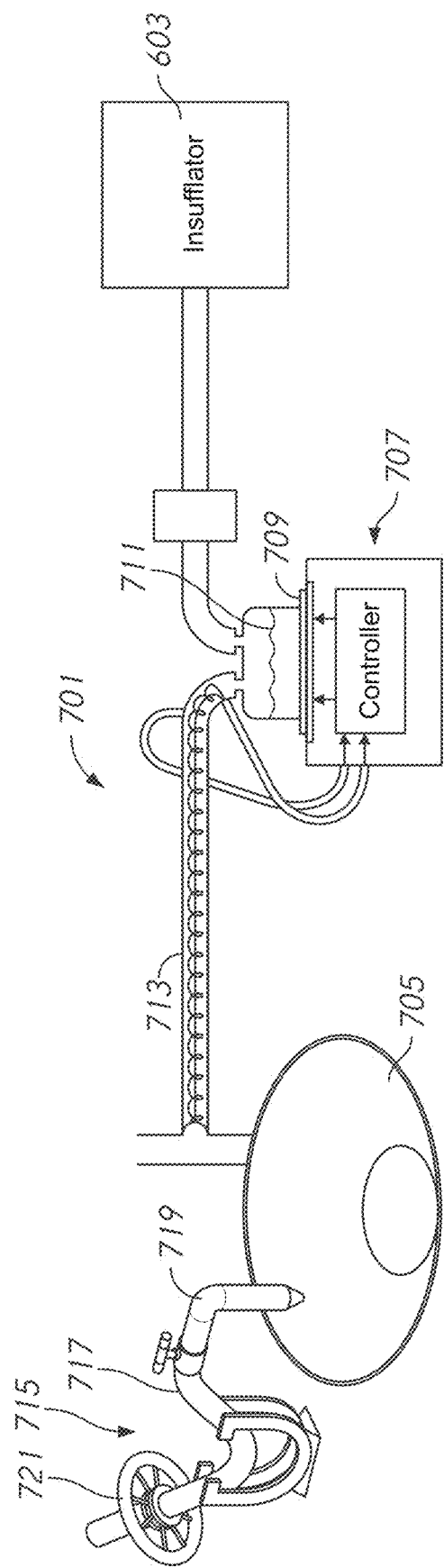
FIG. 7 schematically shows an example insufflation system.

Reference is next made to FIG. 7, which shows an insufflation system 701. The insufflation system 701 includes an insufflator 603 that produces a stream of insufflation gases at a pressure above atmospheric for delivery into the patient's 705 abdominal or peritoneal cavity. The gases pass into a humidifier 707, which includes a heater base 709 and humidifier chamber 711. In use, the chamber 711 is in contact with the heater base 709 so that the heater base 709 provides heat to the chamber 711. In the humidifier 707, the insufflation gases are passed through the chamber 711 so that the gases become humidified to an appropriate level of moisture for delivery to the patient.

The system 701 includes a delivery conduit 713 that connects between the humidifier chamber 711 and the patient's 705 peritoneal cavity or surgical site. The conduit 713 has a first end and a second end. The first end can be connected to the outlet of the humidifier chamber 711 and receive humidified gases from the chamber 711. The second end of the conduit 713 can be placed in the patient's 705 surgical site or peritoneal cavity. Humidified insufflation gases travel from the chamber 711, through the conduit 713 and into the surgical site to insufflate and expand the surgical site or peritoneal cavity. The system 701 also includes a controller that regulates the amount of humidity supplied to the gases by controlling the power supplied to the heater base 709. The controller can also be used to monitor water level in the humidifier chamber 711. A smoke evacuation system 715 is shown leading out of the body cavity of the patient 705.

The smoke evacuation system 715 can be used in conjunction with the insufflation system 701 described above or may be used with other suitable insufflation systems. The smoke evacuation system 715 comprises a discharge or exhaust limb 717, a discharge assembly 719, and a filter 721. The discharge limb 717 connects between the filter 721 and the discharge assembly 719. The discharge assembly 719, when in use, is located in or adjacent to the patient's 705 surgical site or peritoneal cavity. The discharge limb 717 is a self-supporting tube (that is, the tube is capable of supporting its own weight without collapsing) with two open ends: an operative site end and an outlet end.

The composite tube described herein can be used as the conduit 713 to deliver humidified gases to the patient's 705 surgical site. The composite tube can deliver humidified gases with minimized heat loss. This can advantageously reduce overall energy consumption in the insufflation system, because less heat input is needed to compensate for heat loss.

Coaxial Tube

A coaxial breathing tube can also comprise a composite tube as described above. In a coaxial breathing tube, a first gas space is an inspiratory limb or an expiratory limb, and the second gas space is the other of the inspiratory limb or expiratory limb. One gas passageway is provided between the inlet of said inspiratory limb and the outlet of said inspiratory limb, and one gas passageway is provided between the inlet of said expiratory limb and the outlet of said expiratory limb. The first gas space can be the inspiratory limb, and the second gas space can be the expiratory limb. Alternatively, the first gas space can be the expiratory limb, and the second gas space can be the inspiratory limb.

Figure 8:
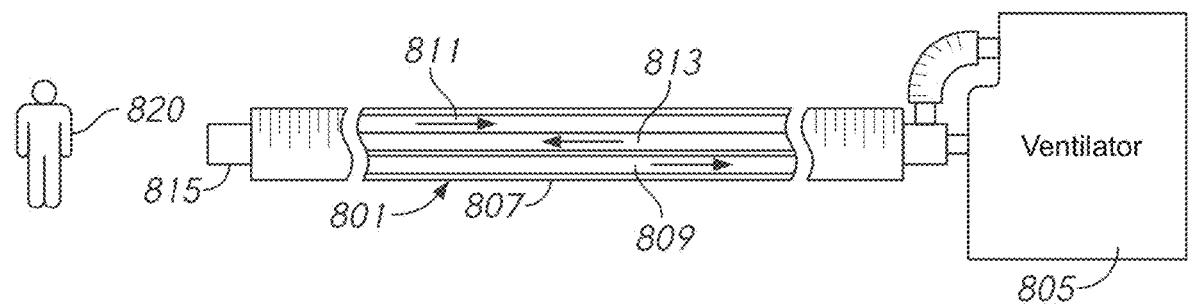
FIG. 8 is a schematic illustration of an example coaxial tube.

Reference is next made to FIG. 8, which shows a coaxial tube 801. In this example, the coaxial tube 801 is provided between a patient 820 and a ventilator 805. Expiratory gases and inspiratory gases each flow in one of the inner tube 807 or the space 809 between the inner tube 807 and the outer tube 811. It will be appreciated that the outer tube 811 may not be exactly aligned with the inner tube 807. Rather, "coaxial" refers to a tube situated inside another tube.

For heat transfer reasons, the inner tube 807 can carry the inspiratory gases in the space 813 therewithin, while the expiratory gases are carried in the space 809 between the inner tube 807 and the outer tube 811. This airflow configuration is indicated by arrows. However, a reverse configuration is also possible, in which the outer tube 811 carries inspiratory gases and the inner tube 807 carries expiratory gases.

The inner tube 807 can be formed from a corrugated tube, such as a Fisher & Paykel model RT100 disposable tube. The outer tube 811 can be formed from a composite tube, as described above.

With a coaxial tube 801, it may be difficult to detect a leak in the inner tube 807. Such a leak may short circuit the patient 820, meaning that the patient 820 will not be supplied with sufficient oxygen. Such a short circuit may be detected by placement of a sensor at the patient end of the coaxial tube 801. This sensor may be located in the patient end connector 815. A short circuit closer to the ventilator 805 will lead to continued patient 820 re-breathing of the air volume close to the patient 820. This will lead to a rise in the concentration of carbon dioxide in the inspiratory flow space 813 close to the patient 801, which can be detected directly by a $CO_2$ sensor. Such a sensor may comprise any one of a number of such sensors as is currently commercially available. Alternatively, this re-breathing may be detected by monitoring the temperature of the gases at the patient end connector 815, wherein a rise in temperature above a predetermined level indicates that re-breathing is occurring.

In addition, to reduce or eliminate the formation of condensation within either the inner tube 807 or outer tube 811, and to maintain a substantially uniform temperature in the gases flow through the coaxial tube 801, a heater, such as a resistance heater filament, may be provided within either the inner tube 807 or outer tube 811, disposed within the gases spaces 809 or 813, or within the inner tube 807 or outer tube 811 walls themselves.

Thermal Properties

In a composite tube, such as the tube 201 incorporating a heating filament 215, heat can be lost through the walls of the first elongate member 203, resulting in uneven heating. As explained above, one way to compensate for these heat losses is to apply an external heating source at the first elongate member 203 walls, which helps to regulate the temperature and counter the heat loss. Other methods for optimizing thermal properties can also be used.

Reference is next made to FIGS. 9A through 9C, which demonstrate example configurations for bubble height (that is, the cross-sectional height of the first elongate member 203 measured from the surface facing the inner lumen to the surface forming the maximum outer diameter) to improve thermal properties.

The dimensions of the bubble can be selected to reduce heat loss from the composite tube 201. Generally, increasing the height of the bubble increases the effective thermal resistance of the tube 201, because a larger bubble height permits the first elongate member 203 to hold more insulating air. However, it was discovered that, at a certain bubble height, changes in air density can cause convection inside the tube 201, thereby increasing heat loss. Also, at a certain bubble height, the surface area becomes so large that the heat lost through surface outweighs the benefits of the increased height of the bubble.

The radius of curvature and the curvature of the bubble can also be useful for determining a desirable bubble height. The curvature of an object is defined as the inverse of the radius of curvature of that object. Therefore, the larger a radius of curvature an object has, the less curved the object is. For example, a flat surface would have a radius of curvature of ∞, and therefore a curvature of 0.

FIG. 9A shows a longitudinal cross-section of a top portion of a composite tube. FIG. 9A shows an example composite tube 201 where the bubble has a large height. In this example, the bubble has a relatively small radius of curvature and therefore a large curvature. Also, the bubble is approximately three to four times greater in height than the height of the second elongate member 205.

FIG. 9B shows a longitudinal cross-section of a top portion of another composite tube. FIG. 9B shows an example composite tube 201 where the bubble is flattened on top. In this example, the bubble has a very large radius of curvature but a small curvature. Also, the bubble is approximately the same height as the second elongate member 205.

FIG. 9C shows a longitudinal cross-section of a top portion of another composite tube. FIG. 9C shows an example composite tube 201 where the width of the bubble is greater than the height of the bubble. In this example, the bubble has radius of curvature and the curvature between that of FIG. 9A and FIG. 9B. The center of the radius for the upper portion of the bubble is outside of the bubble (as compared to FIG. 9A). The inflection points on the left and right sides of the bubble are about at the middle (heightwise) of the bubble (as opposed to in the lower portion of the bubble, as in FIG. 9A). Also, the height of the bubble is approximately double that of the second elongate member 205, resulting in a bubble height between that of FIG. 9A and FIG. 9B.

The configuration of FIG. 9A resulted in the lowest heat loss from the tube. The configuration of FIG. 9B resulted in the highest heat loss from the tube. The configuration of FIG. 9C had intermediate heat loss between the configurations of FIGS. 9A and 9B. However, the large external surface area and convective heat transfer in the configuration of FIG. 9A can lead to inefficient heating. Thus, of the three bubble arrangements of FIGS. 9A-9C, FIG. 9C was determined to have the best overall thermal properties. When the same thermal energy was input to the three tubes, the configuration of FIG. 9C allowed for the largest temperature rise along the length of the tube. The bubble of FIG. 9C is sufficiently large to increase the insulating air volume, but not large enough to cause a significant convective heat loss. The configuration of FIG. 9B was determined to have the poorest thermal properties, namely that the configuration of FIG. 9B allowed for the smallest temperature rise along the length of the tube. The configuration of FIG. 9A had intermediate thermal properties and allowed for a lower temperature rise than the configuration of FIG. 9C.

It should be appreciated that although the FIG. 9C configuration may be preferred, other configurations, including those of FIGS. 9A, 9B and other variations, may also be utilized as may be desired.

TABLE 7 shows the height of the bubble, the outer diameter of the tube, and the radius of curvature of the configurations shown in each of FIGS. 9A, 9B, and 9C.

TABLE 7

| Tube (FIG.) | 9A | 9B | 9C |
| --- | --- | --- | --- |
| Bubble height (mm) | 3.5 | 5.25 | 1.75 |
| Outer diameter (mm) | 21.5 | 23.25 | 19.75 |
| Radius of curvature (mm) | 5.4 | 3.3 | 24.3 |

Figure 11A:
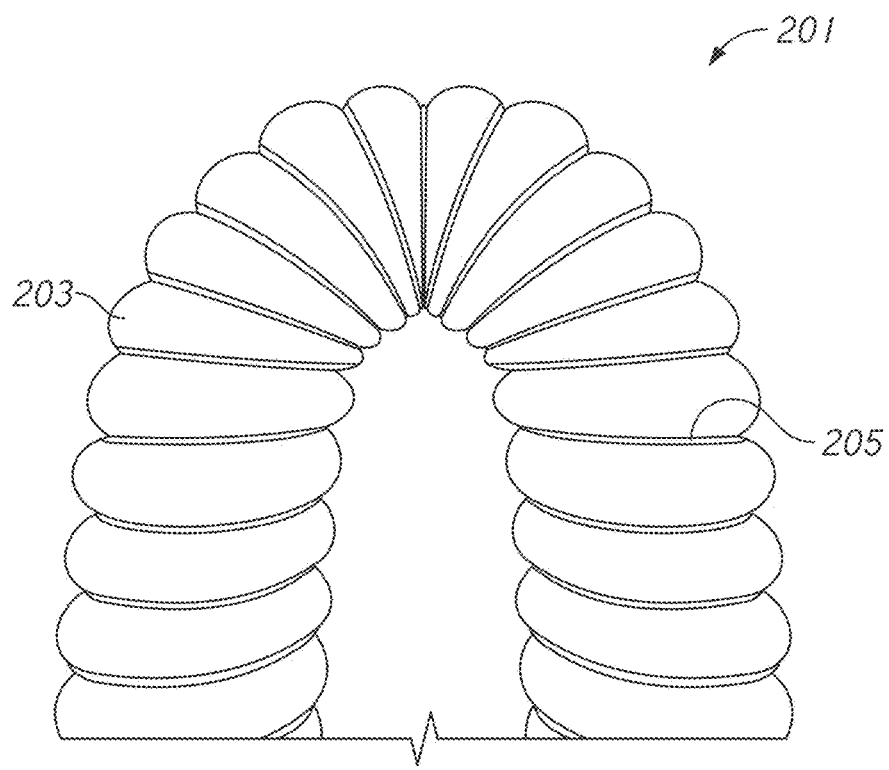
FIGS. 11A-D demonstrate radius of curvature properties of tubes.
Figure 11B:
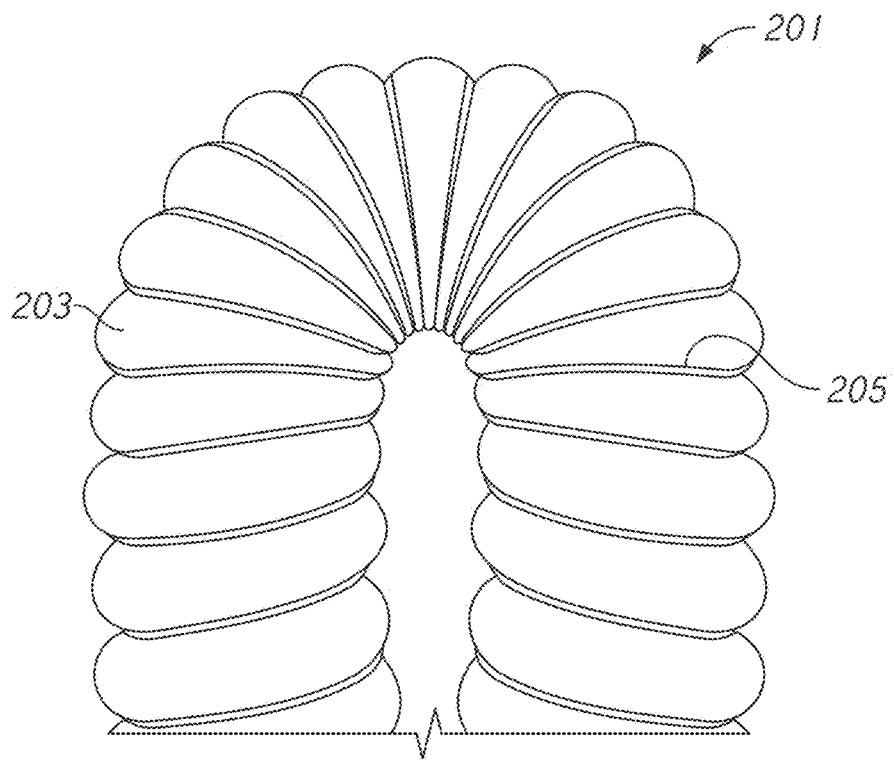
Figure 11C:
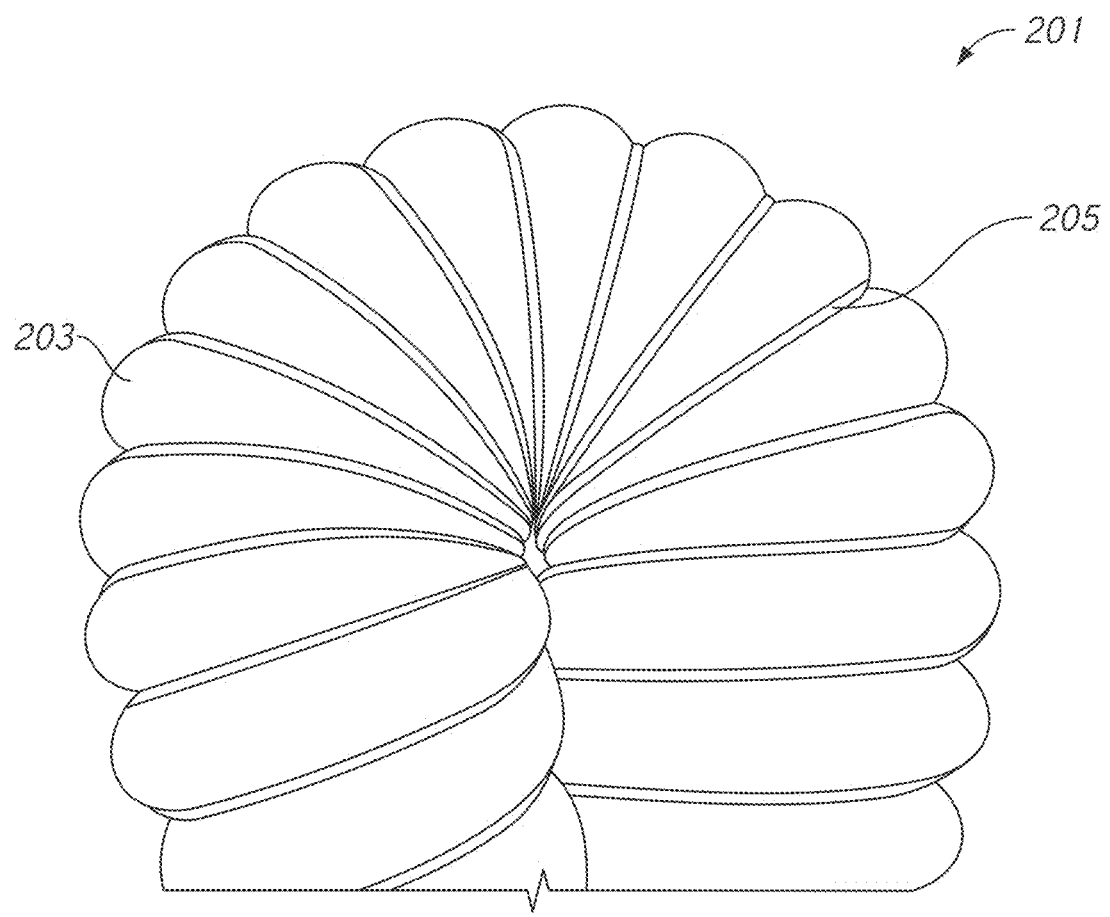

TABLE 7A shows the height of the bubble, the outer diameter and the radius of curvature of further configurations as shown in FIGS. 11A, 11B, and 11C.

TABLE 7A

| Tube (FIG.) | 11A | 11B | 11C |
| --- | --- | --- | --- |
| Bubble height (mm) | 6.6 | 8.4 | 9.3 |
| Outer diameter (mm) | 24.6 | 26.4 | 27.3 |
| Radius of curvature (mm) | 10 | 8.7 | 5.7 |

Figure 11D:
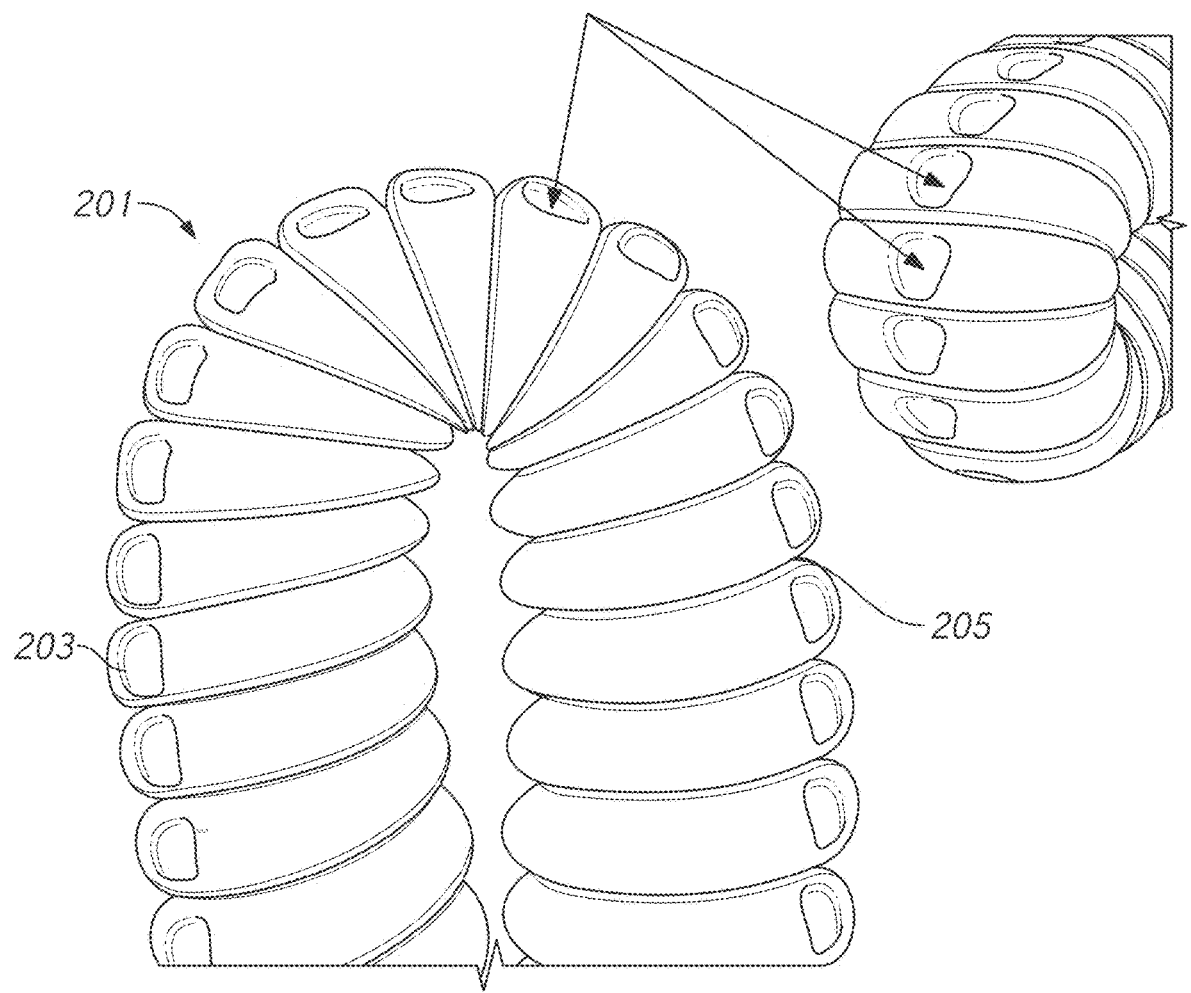

It should be noted that, in general, the smaller the radius of curvature, the tighter the tube can be bent around itself without the bubble collapsing or "kinking." For example, FIG. 11D shows a tube that has been bent beyond its radius of curvature (specifically, it shows the tube of FIG. 11A bent around a radius of curvature of 5.7 mm), thereby causing kinking in the walls of the bubble. Kinking is generally undesirable, as it can detract from the appearance of the tube, and can impair the thermal properties of the tube.

Accordingly, configurations with increased bending properties (such as those shown in FIG. 9A or 9B) can be desirable despite having less efficient thermal properties. In some applications, it has been found that a tube with an outer diameter of 25 mm to 26 mm (or about 25 mm to about 25 mm) provides a good balance between thermal efficiency, flexibility, and bending performance. It should be appreciated that although the configurations of FIGS. 9A and 9B may be preferred, other configurations, including those of FIGS. 11A-11D and other variations, may also be utilized as may be desired.

Reference is next made to FIGS. 9C through 9F which demonstrate example positioning of heating element 215 with similar bubble shapes to improve thermal properties. The location of the heating element 215 can change the thermal properties within the composite tube 201.

FIG. 9C shows a longitudinal cross-section of a top portion of another composite tube. FIG. 9C shows an example composite tube 201 where the heating elements 215 are centrally located in the second elongate member 205. This example shows the heating elements 215 close to one another and not close to the bubble wall.

Figure 9D:
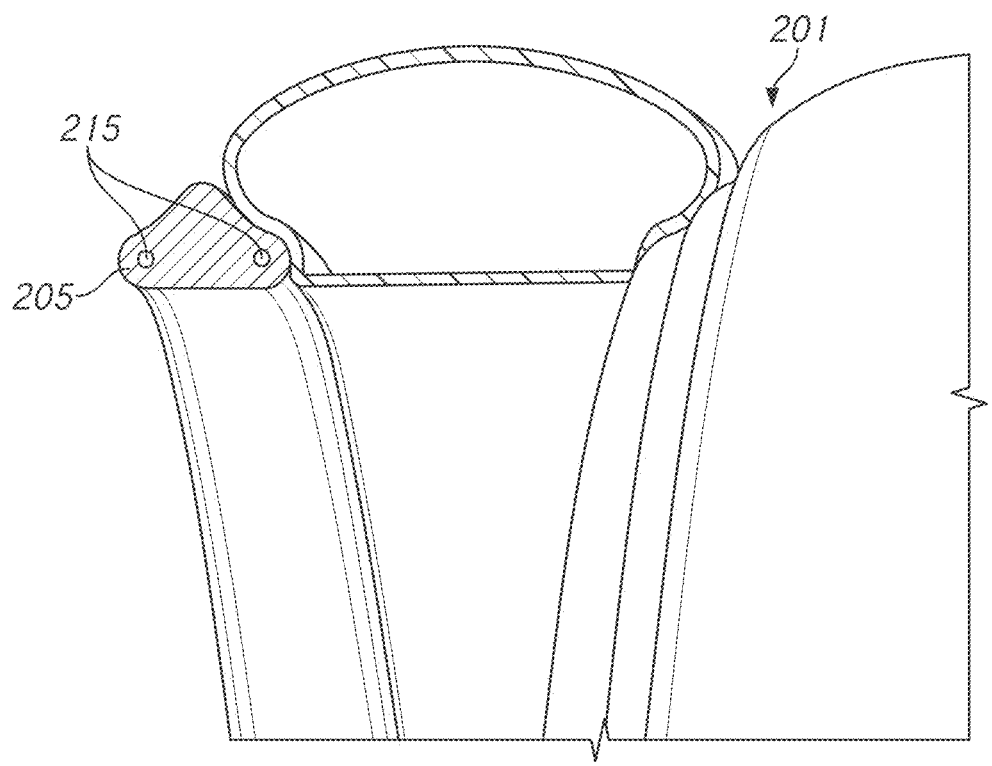
FIGS. 9D-F show examples of filament arrangements configured to improve thermal efficiency.

FIG. 9D shows a longitudinal cross-section of a top portion of another composite tube. FIG. 9D shows an example composite tube 201 in which the heating elements 215 are spaced farther apart, as compared to FIG. 9C, in the second elongate member 205. These heating elements are closer to the bubble wall and provide for better regulation of heat within the composite tube 201.

Figure 9E:
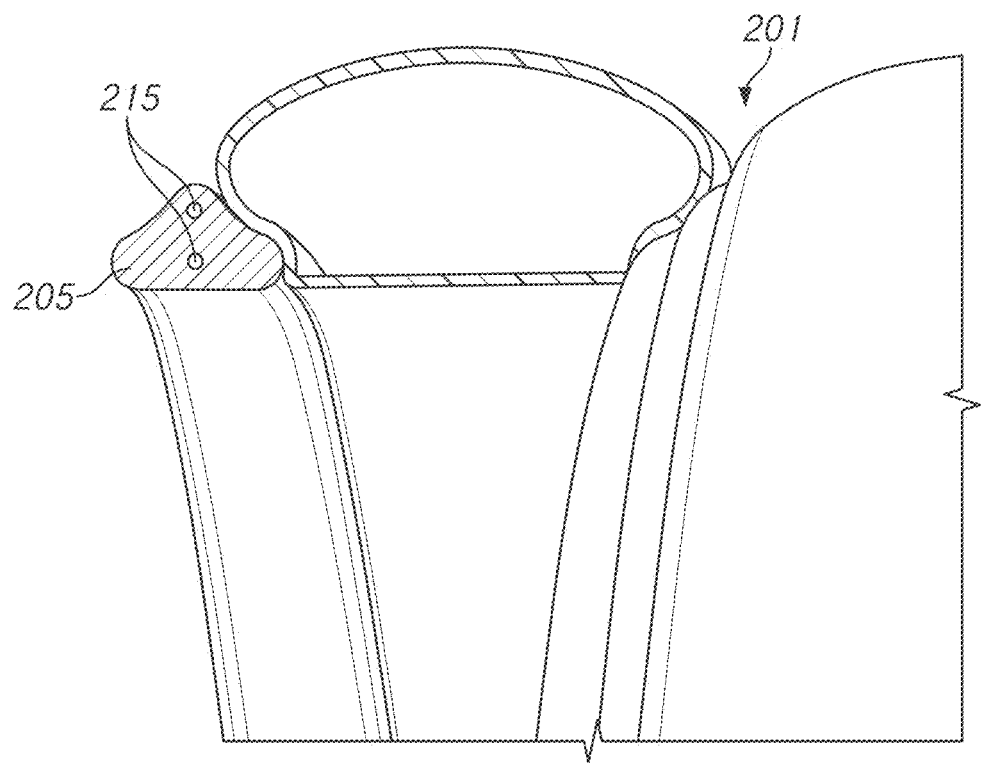

FIG. 9E shows a longitudinal cross-section of a top portion of another composite tube. FIG. 9E shows an example composite tube 201 wherein the heating elements 215 are spaced on top of each other in the vertical axis of the second elongate member 205. In this example, the heating elements 215 are equally close to each bubble wall.

Figure 9F:
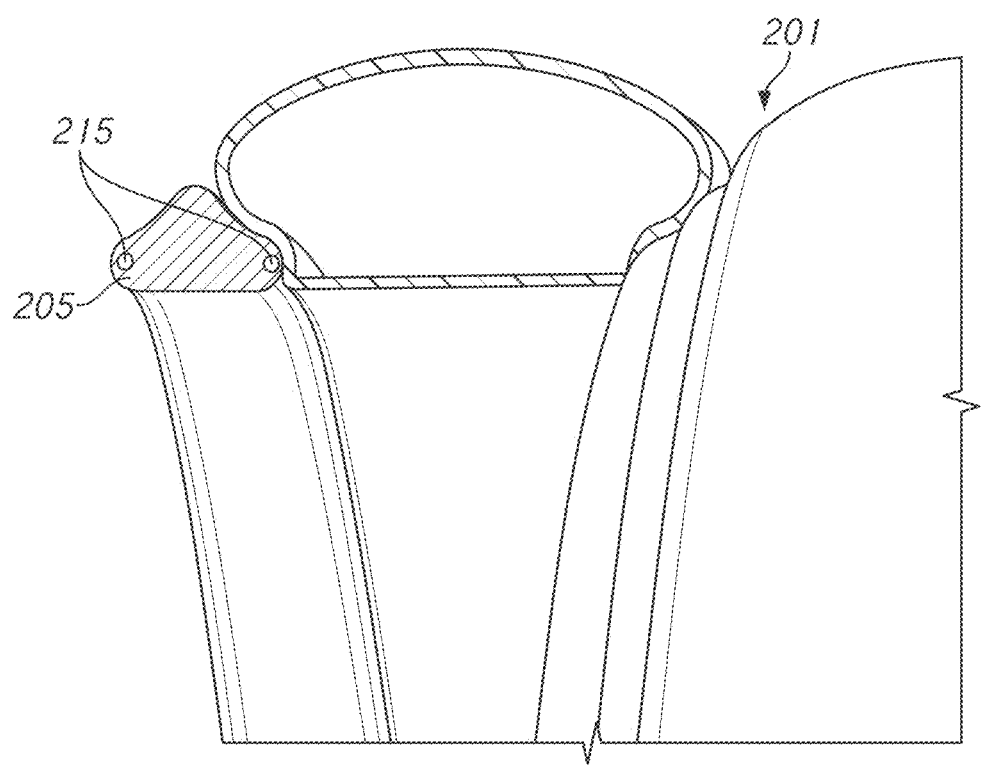

FIG. 9F shows a longitudinal cross-section of a top portion of another composite tube. FIG. 9F shows example composite tube 201 where the heating elements 215 are spaced at opposite ends of the second elongate member 205. The heating elements 215 are close to the bubble wall, as compared to FIGS. 9C-9E.

Of the four filament arrangements of FIGS. 9C-9F, FIG. 9F was determined to have the best thermal properties. Because of their similar bubble shapes, all of the configurations of FIGS. 9C-9F experienced similar heat loss from the tube. However, when the same thermal energy was input to the tubes, the filament configuration of FIG. 9F allowed for the largest temperature rise along the length of the tube. The configuration of FIG. 9D was determined to have the next best thermal properties and allowed for the next largest temperature rise along the length of tube. The configuration of FIG. 9C performed next best. The configuration of FIG. 9E had the poorest performance and allowed for the smallest temperature rise along the length of the tube, when the same amount of heat was input.

It should be appreciated that although the FIG. 9F configuration may be preferred, other configurations, including those of FIGS. 9C, 9D, 9E, and other variations, may also be utilized as may be desired.

Figure 9G:
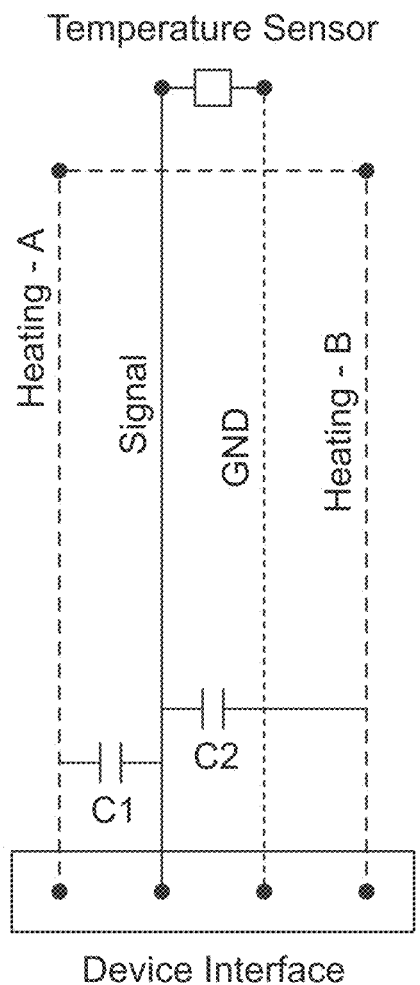
FIGS. 9G-L show examples of filament arrangements including heating wires and sensor wires.

FIGS. 9G-L illustrate various filament (also referred to herein as "wire") arrangements in a tube. In these arrangements, both heating wires, sensor and ground wires are included in the arrangement. The heating wires in combination with a temperature sensor and associated wiring enable fine control of air temperature. FIG. 9G illustrates an example wire arrangement in which two heater wires A and B are spaced apart as far as possible with a sensor wire and a ground wire located between the heater wires. As discussed with respect to FIGS. 3G and 9F, it is advantageous to space the heating wires as far apart as possible for better heating performance. Additionally, this configuration provides a lower risk of heating wires sparking as a result of larger distances between the heating wires.

Figure 9H:
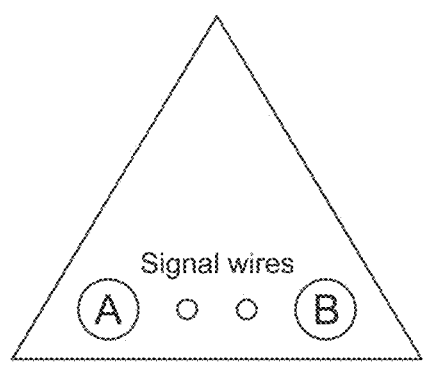

It has been discovered, however, that with increased lengths of tubing and closer proximity of heating and sensor wires, increased electrical interference between the temperature sensing signal wire and the heating wires develops. This increased electrical interference leads to incorrect sensor measurements. For example, in tubing with lengths of about 1.5 meters or greater, or about 1.6 meters or greater, or about 1.75 meters or greater, or about 1.8 meters or greater, or about 2.4 meters or greater, alternating current at mains power frequency in the heating wires creates a capacitive effect on the sensor wire leading to errors in the temperature measurements from the inbuilt temperature sensor in the circuit. The heater wires in the tubes described herein can have lengths of, for example, about 20 meters to about 50 meters, or about 25 meters to about 40 meters, or about 25 meters to about 26 meters, or about 40 meters. The sensor wire can run along next to the heater wires. The heater wire length and/or sensor wire length can be affected by the pitch of the windings during manufacturing. The tighter the pitch and/or the larger the diameter of the mandrel, the longer are the heater wires and/or the sensor wire. The relatively large length of wire coiled in the tubing and a relatively small separation gap between the wires effectively creates a small capacitor significant enough to affect the temperature measurement system. The longer the heater wires and/or sensor wires, the greater is the capacitive coupling effect. Referring to FIGS. 9G and 9H, the signal wire in the illustrated arrangement experienced coupling with both the A and B heating wires (the effect of which is illustrated by capacitances C1 and C2, which it is to be understood are not physical capacitors, but rather only conceptual illustrations of the capacitive effects). The effects from these couplings are anti-phased, as currents A and B flow in opposite directions and follow the principle of superposition. The net signal voltage read by the device can be expressed as $$V_{signal} = V_{Thermistor} + V_{coupled\ A} + V_{coupled\ B}$$

where $V_{coupled\ A}$ and $V_{coupled\ B}$ are opposite in sign due to A and B being anti-phase.

As the A wire is closer to the signal wire than the B wire, the A-signal capacitance is larger, (C1>C2). This is observed as a stronger coupling of the A wire to the signal wire. As a result:

$$|V_{coupled\ A}| > |V_{coupled\ B}| \therefore V_{noise} = V_{coupled\ A} + V_{coupled\ B} \neq 0$$

As $V_{coupled\ A}$ and $V_{coupled\ B}$ are supplied by mains frequency, the unequal voltage occurs on the signal as 50 Hz noise. With increased length, there is a significant increase in capacitances C1 and C2; and therefore the coupled noise.

Solutions are identified as spacing the wires, offsetting the measurement system for the known noise, adding a compensation capacitor to reduce the difference in capacitance and altering the wire arrangement, or any combination of the foregoing. The solutions can benefit tubes of any length as the capacitive coupling occurs in tubes of any length.

Wire spacing distance may be limited by the tube arrangement. One solution to compensate for the noise is to incorporate a heating wires voltage feedback into the temperature measurement system. However, this can be complex and costly to implement and may be undesirable.

Figure 9I:
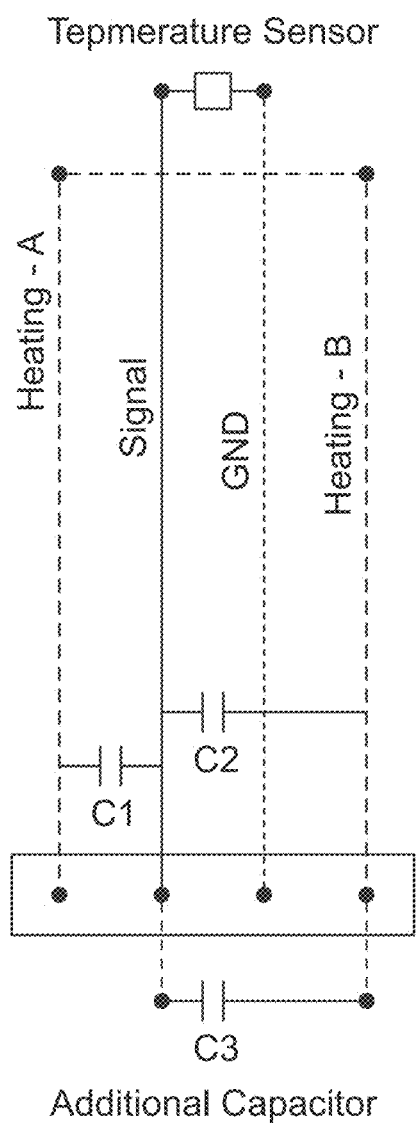

Another solution is to add a physical capacitor between the B heating wire and signal wire, for example, as shown in FIG. 9I. Adding a physical capacitor, C3, parallel to the B heating wire to signal wire capacitance C2 may equalize the difference in capacitance between C1 and C2, (C1=C2+C3). This may make the capacitive coupling to each wire equally strong. After addition of the capacitor C3, heating wires A and B will still interfere with the signal wire, but the net effect can be destructive, and/or the net effect can be nominally zero. This removes most of the noise in the system and improves signal measurement accuracy. This solution involves a small increase in cost and an additional manufacturing step and may involve individual calibration.

Figure 9J:
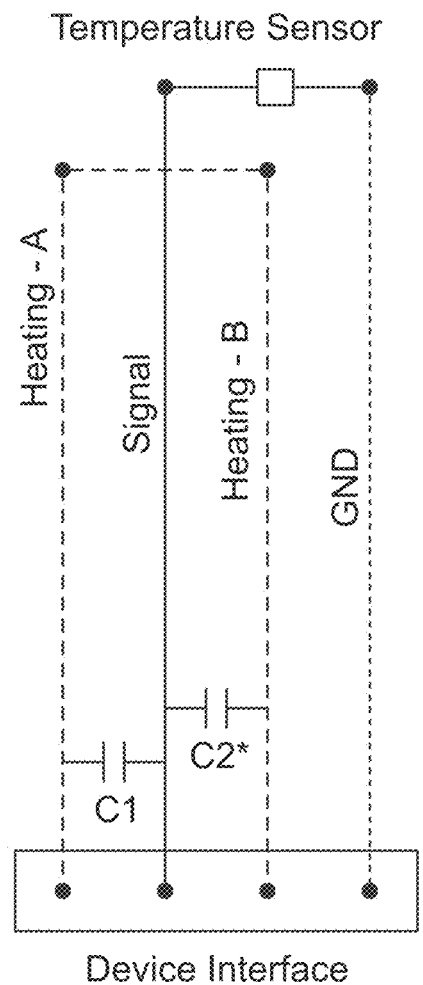
Figure 9K:
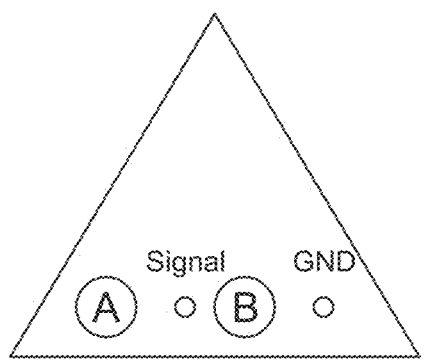

Another solution is to swap the locations of the B heating wire and the GND wire, for example, as shown in FIGS. 9J and 9K. In the resulting arrangement, the A and B heating wires are equidistant from the signal wire. The effective capacitance between the signal wire and the B heating wire increases as compared with the configurations in FIGS. 9G-9I. As a result, the capacitances are equal, C1=C2*, and there is equally strong coupling between the signal wire and each heater wire. This results in cancellation of noise, similar to the previously mentioned solution. While there is still unequal coupling occurring on the GND wire, this has been found to not affect the sensor system design, as the GND signal has lower impedance than the sensor wire. The lower impedance results in capacitive coupling on the GND wire having minimal effect on its voltage, as opposed to the effect of capacitive coupling on the voltage of the sensor wire.

Figure 9L:
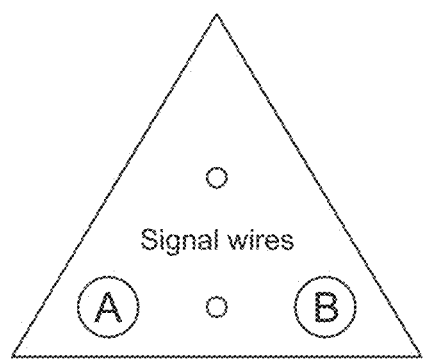

Multiple configurations for the wires are possible and fall within the scope of the present disclosure. For example, other configurations that allow for equal capacitive coupling between the heating wires and the sensor wires are possible. An alternative design is shown in FIG. 9L, which also reduces noise on the GND wire and still has maximum displacement between the two heating tubes. In FIG. 9L, the GND wire and the sensor wire can be equidistant between the heater wires A and B and stacked in a vertical or substantially vertical arrangement. The GND wire can be on top of the sensor wire, or the sensor wire can be on top of the GND wire. Other wire configurations can also be used to allow the sensor wire to be equidistant from the two heater wires. For example, the wires can be arranged generally horizontally in the order of the GND wire, the heater wire A or B, the sensor wire, and the heater wire B or A. This arrangement can be a mirror image of the arrangement in FIGS. 9J and 9K.

Although the present disclosure is described mainly with respect to the bubble tube arrangement provided herein, it is to be understood that solutions provided to the capacitive coupling effect described are applicable to any tubes of any lengths having closely spaced heating wire and sensor wire configurations. Accordingly, the present disclosure is not to be limited to the particular tube configuration, but rather extends to any tube configurations that include closely spaced wire configurations.

Figure 10A:
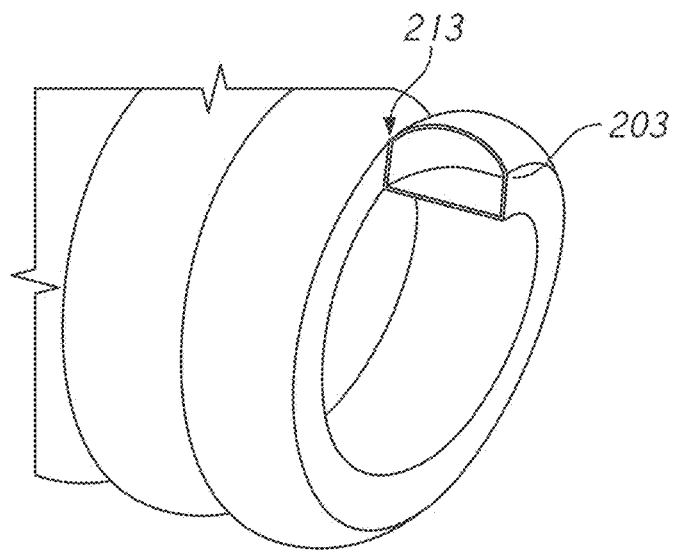
FIGS. 10A-C show examples of first elongate member stacking.
Figure 10B:
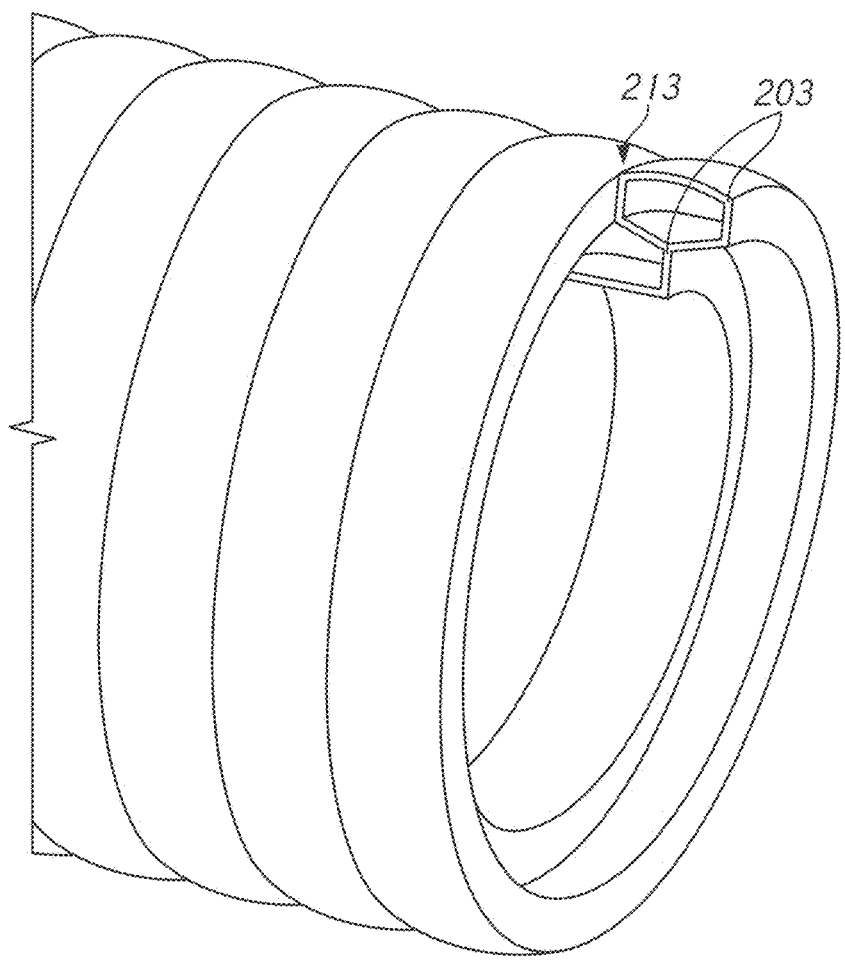
Figure 10C:
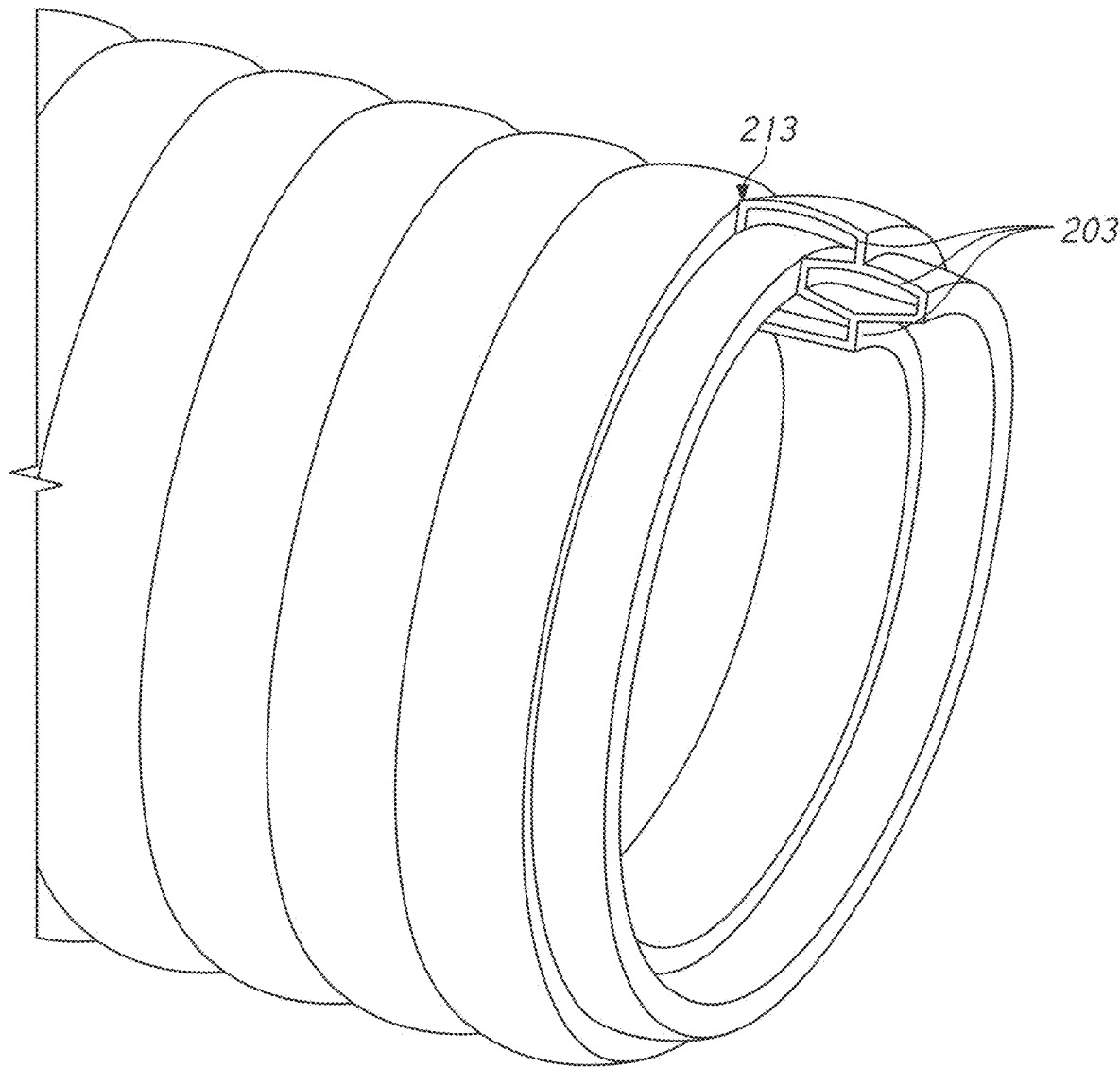

Reference is next made to FIGS. 10A through 10C, which demonstrate example configurations for stacking of the first elongate member 203. It was discovered that heat distribution can be improved by stacking multiple bubbles. These stacking can be more beneficial when using an internal heating filament 215. FIG. 10A shows a longitudinal cross-section of a top portion of another composite tube. FIG. 10A shows a cross section of a composite tube 201 without any stacking.

FIG. 10B shows a longitudinal cross-section of a top portion of another composite tube. FIG. 10B shows another example composite tube 201 with stacked bubbles. In this example, two bubbles are stacked on top of each other to form the first elongate member 203. As compared to FIG. 10A, the total bubble height is maintained, but the bubble pitch is half of FIG. 10A. Also, the tube 201 in FIG. 10B has only a slight reduction in air volume. The stacking of the bubbles reduces natural convection and heat transfer in the gap between bubbles 213 and lowers the overall thermal resistance. The heat flow path increases in the stacked bubbles allowing heat to more easily distribute through the composite tube 201.

FIG. 10C shows a longitudinal cross-section of a top portion of another composite tube. FIG. 10C shows another example of a composite tube 201 with stacked bubbles. In this example, three bubbles are stacked on top of each other to form the first elongate member 203. As compared to FIG. 10A, the total bubble height is maintained, but the bubble pitch is a third of FIG. 10A. Also, the tube 201 in FIG. 10B has only a slight reduction in air volume. The stacking of the bubbles reduces natural convection and heat transfer in the gap between bubbles 213.

Tube Information

The tubes and/or other associated components described herein can include an information element. The information element can identify characteristics of the tube(s) and/or peripheral components coupled to the information element, such as arrangements and/or wire configurations of the tubes described herein. The information element can be a resistor or a thermistor measuring a resistance of a wire on or in the tube or associated components. The tube information identified by the information element can be provided to a controller or processor via wired and/or wireless communications. The controller or processor can calibrate sensor measurements, and/or change modes and/or operational parameters based at least in part on the received tube information. Other examples of an information element can include, but are not limited to, an EPROM, an RF information element, a bar code, and the like.

Cleaning

Materials for a composite tube can be selected to handle various methods of cleaning. High level disinfection (around 20 cleaning cycles) can be used to clean the composite tube, such as the tube 201. During high level disinfection, the composite tube 201 is subject to pasteurization at about 75° C. for about 30 minutes. Next, the composite tube 201 is bathed in 2% glutaraldehyde for about 20 minutes. The composite tube 201 is removed from the glutaraldehyde and submerged in 6% hydrogen peroxide for about 30 minutes. Finally, the composite tube 201 is removed from the hydrogen peroxide and bathed in 0.55% orthophthalaldehyde (OPA) for about 10 minutes.

Sterilization (around 20 cycles) can also be used to clean the composite tube 201. First, the composite tube 201 is placed within autoclave steam at about 121° C. for about 30 minutes. Next, the temperature of the autoclave steam is increased to about 134° C. for about 3 minutes. After autoclaving, the composite tube 201 is surrounded by 100% ethylene oxide (ETO) gas. Finally, the composite tube 201 is removed from the ETO gas and submerged in about 2.5% glutaraldehyde for about 10 hours.

The composite tube 201 may be made of materials to withstand the repeated cleaning process. Part or all of the composite tube 201 can be made of, but is not limited to, styrene-ethylene-butene-styrene block thermo plastic elastomers, for example Kraiburg TF6STE. The composite tube 201 can also be made of, but is not limited to, hytrel, urethanes, or silicones.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The foregoing description of the invention includes preferred forms thereof. Modifications may be made thereto without departing from the scope of the invention. To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A tube for conveying humidified gases to a patient, the tube comprising:
   first and second heating wires traversing at least a portion of the length of the tube; and
   a sensor wire in electrical communication with a temperature sensor;
   wherein the first and second heating wires and the sensor wire are arranged in close proximity within the tube and the first and second heating wires are spaced equal distance from the sensor wire.

2. The tube of claim 1, wherein the first and second heating wires and the sensor wire are all located along a line on a longitudinal cross-sectional plane of the tube.

3. The tube of claim 2, wherein the first and second heating wires and the sensor wire are located along a line substantially parallel to a longitudinal axis of the tube in the longitudinal cross-sectional plane of the tube.

4. The tube of claim 1, wherein the first heating wire is located on a first side of the sensor wire and the second heating wire is located on a second side of the sensor wire.

5. The tube of claim 1, further comprising a ground wire.

6. The tube of claim 5, wherein the first and second heating wires are spaced equal distance from both the sensor wire and the ground wire.

7. The tube of claim 5, wherein the sensor wire is between the first and second heating wires, and the ground wire is on an opposite side of the first or second heating wire as the sensor wire.

8. The tube of claim 5, wherein the sensor wire and the ground wire are between the first and second heating wires.

9. The tube of claim 8, wherein the sensor wire and the ground wire are arranged substantially vertically in the longitudinal cross-sectional plane of the tube.

10. The tube of claim 1, wherein the tube has a length of greater than 1.5 meters.

11. The tube of claim 1, wherein the tube comprises:
    a first elongate member comprising a hollow body spirally wound to form at least in part an elongate tube having a longitudinal axis, a lumen extending along the longitudinal axis, and a hollow wall at least partially surrounding the lumen; and
    a second elongate member spirally wound and joined between adjacent turns of the first elongate member, the second elongate member forming at least a portion of the lumen of the elongate tube, wherein the second elongate member acts as a structural support or reinforcement for the first elongate member.

12. The tube of claim 11, wherein portions of the first elongate member overlap adjacent turns of the second elongate member.

13. The tube of claim 11, wherein the first elongate member forms in the longitudinal cross-section a plurality of bubbles, a portion of surfaces of the plurality of bubbles forming the lumen.

14. The tube of claim 13, wherein the plurality of bubbles are adjacent one another.

15. The tube of claim 14, wherein adjacent bubbles are separated by a gap above the second elongate member.

16. The tube of claim 11, wherein the second elongate member has a longitudinal cross-section that is wider proximal the lumen and narrower at a radial distance from the lumen.

17. The tube of claim 16, wherein one or more of the first heater wire, the second heater wire, the sensor wire, and/or the ground wire are embedded or encapsulated in the second elongate member.

18. The tube of claim 17, wherein the second elongate member has a longitudinal cross-section that is generally triangular, generally T-shaped, or generally Y-shaped, and the one or more of the first heater wire, the second heater wire, the sensor wire, and/or the ground wire are embedded or encapsulated in the second elongate member on opposite sides of the triangle, T-shape, or Y-shape.

19. The tube of claim 1, wherein the tube comprises:
   an elongate hollow body spirally wound to form an elongate tube having a longitudinal axis, a lumen extending along the longitudinal axis, and a hollow wall surrounding the lumen, wherein the elongate hollow body has in transverse cross-section a wall defining at least a portion of the hollow body; and
   a reinforcement portion extending along a length of the elongate hollow body being spirally positioned between adjacent turns of the elongate hollow body, wherein the reinforcement portion forms a portion of the lumen of the elongate tube;
   wherein the reinforcement portion forms a portion of the lumen of the elongate tube;
   wherein the reinforcement portion is relatively thicker or more rigid than the wall of the elongate hollow body, and
   wherein the reinforcement portion is formed from the same place of material as the elongate hollow body.

20. The tube of claim 19, wherein the elongate hollow body in a longitudinal cross-section of the tube comprises two reinforcement portions on opposite sides of the elongate hollow body, wherein spiral winding of the elongate hollow body joins adjacent reinforcement portions to each other such that opposite edges of the reinforcement portions touch on adjacent turns of the elongate hollow body.

21. The tube of claim 19, wherein the hollow body forms in a longitudinal cross-section of the tube a plurality of bubbles, a portion of surfaces of the plurality of bubbles forming the lumen.

22. The tube of claim 19, wherein one or more of the first heater wire, the second heater wire, the sensor wire, and/or the ground wire are embedded or encapsulated within the reinforcement portion.

23. A tube for conveying humidified gases to a patient, the tube comprising:
   a first elongate member comprising a hollow body spirally wound to form at least in part an elongate tube having a longitudinal axis, a lumen extending along the longitudinal axis, and a hollow wall at least partially surrounding the lumen; and
   a second elongate member spirally wound and joined between adjacent turns of the first elongate member, the second elongate member forming at least a portion of the lumen of the elongate tube, wherein the second elongate member acts as a structural support or reinforcement for the first elongate member,
   wherein the second elongate member comprises first and second heating wires and a sensor wire, the sensor wire in electrical communication with a temperature sensor; and
   wherein the first and second heating wires and the sensor wire are arranged in close proximity within the second elongate member and the first and second heating wires are spaced equal distance from the sensor wire.

24. The tube of claim 23, wherein the first heating wire is located on a first side of the sensor wire and the second heating wire is located on a second side of the sensor wire.

25. The tube of claim 23, further comprising a ground wire.

26. The tube of claim 25, wherein the first and second heating wires are spaced equal distance from both the sensor wire and the ground wire.

27. The tube of claim 25, wherein the sensor wire is between the first and second heating wires, and the ground wire is on an opposite side of the first or second heating wire as the sensor wire.

28. The tube of claim 25, wherein the second elongate member is generally triangular in shape, and at least two of the first heater wire, the second heater wire, the sensor wire, or the ground wire are embedded or encapsulated in the second elongate member on opposite sides of the triangle.

* * * * *